(12) United States Patent
Garfield et al.

(10) Patent No.: US 6,816,744 B2
(45) Date of Patent: Nov. 9, 2004

(54) DEVICE AND SYSTEM FOR REMOTE FOR IN-CLINIC TRANS-ABDOMINAL/VAGINAL/CERVICAL ACQUISITION, AND DETECTION, ANALYSIS, AND COMMUNICATION OF MATERNAL UTERINE AND MATERNAL AND FETAL CARDIAC AND FETAL BRAIN ACTIVITY FROM ELECTRICAL SIGNALS

(75) Inventors: Robert E. Garfield, Friendswood, TX (US); William L. Maner, Galveston, TX (US)

(73) Assignee: Reproductive Health Technologies, Inc., Galveston, TX (US)

( * ) Notice: Subject to any disclaimer, the term of this patent is extended or adjusted under 35 U.S.C. 154(b) by 329 days.

(21) Appl. No.: 10/156,379

(22) Filed: May 28, 2002

(65) Prior Publication Data

US 2002/0193670 A1 Dec. 19, 2002

Related U.S. Application Data

(60) Provisional application No. 60/294,391, filed on May 29, 2001.

(51) Int. Cl.$^7$ ................................................ A61B 5/04
(52) U.S. Cl. ...................... 600/546; 600/304; 600/509; 600/511
(58) Field of Search ................................ 600/544, 546, 600/304, 509, 511

(56) References Cited

U.S. PATENT DOCUMENTS

| | | |
|---|---|---|
| 4,256,118 A | 3/1981 | Nagel |
| 4,308,873 A | 1/1982 | Maynard |
| 4,738,268 A | 4/1988 | Kipnis |
| 5,301,680 A | 4/1994 | Rosenberg |
| 5,397,344 A | 3/1995 | Garfield et al. |
| 5,400,799 A | 3/1995 | Yoches et al. |
| 5,447,526 A | 9/1995 | Karsdon |
| 5,546,953 A | 8/1996 | Garfield |
| 5,581,369 A | 12/1996 | Righter et al. |
| 5,623,939 A | 4/1997 | Garfield |
| 5,776,073 A | 7/1998 | Garfield et al. |
| 5,785,664 A | 7/1998 | Rosenburg |
| 5,791,342 A | 8/1998 | Woodard |
| 5,964,789 A | 10/1999 | Karsdon |
| 5,991,649 A | 11/1999 | Garfield et al. |
| 6,421,558 B1 * | 7/2002 | Huey et al. .................. 600/546 |

* cited by examiner

Primary Examiner—Eric F. Winakur
(74) Attorney, Agent, or Firm—Locke Liddell & Sapp LLP

(57) ABSTRACT

The present invention presents a method and apparatus for recording and analyzing uterine electrical activity, or electromyography (EMG), from the surface of the abdomen, vagina, or cervix of a patient for the purpose of diagnosing contractile patterns of the uterus in pregnant and non-pregnant women, as well as for monitoring maternal and fetal ECG and fetal brain activity. The method and apparatus described include methods for the systematic detection, analysis, characterization and communication of information about electrical signals recorded from the abdominal/vaginal/cervical surface. The present invention provides data analysis techniques for analyzing the electrical data measured from the surface of a patient to characterize their uterine, abdominal, and cardiac muscle activity, as well as cardiac and brain activity of the fetus simultaneously or separately. These techniques and apparatus are appropriate for use in a clinic or through landline or wireless communication for use as a remote or home uterine/fetal monitoring system.

47 Claims, 18 Drawing Sheets

Potential vector P(t)

DEVICE AND SYSTEM FOR REMOTE FOR IN-CLINIC TRANS-ABDOMINAL/VAGINAL/CERVICAL ACQUISITION, AND DETECTION, ANALYSIS, AND COMMUNICATION OF MATERNAL UTERINE AND MATERNAL AND FETAL CARDIAC AND FETAL BRAIN ACTIVITY FROM ELECTRICAL SIGNALS

SPECIFICATION

This application claims the benefit of U.S. Provisional Application Ser. No. 60/294,391, filed May 29, 2001.

FIELD OF THE INVENTION

The present invention relates to measurements of electrical activity in a body. More particularly, the invention relates to measurement and analysis of the measurements to predict the condition of a portion of a body.

BACKGROUND OF THE INVENTION

Presently there is no objective manner with which to evaluate the contractility of the uterus. This is true either in non-pregnant patients where hypercontractility is associated with dysmenorrhea or in pregnant patients where the uterus is sometimes active prior to term. Normally the uterus is quiescent in non-pregnant women and during most of pregnancy. However, at the end of pregnancy, the myometrium undergoes a series of changes that lead to synchronous, rhythmic uterine contractions (labor). The diagnosis of labor is the most significant problem faced by obstetricians. In addition, pre-term labor, which occurs in about 10% of pregnant patients, is difficult to diagnose. Frequently, term or pre-term labor requires adjuvant therapy to either stimulate or inhibit contractility of the uterus.

Since there is some minor spontaneous uterine activity at all times during pregnancy, it is often not possible to distinguish between this physiological activity at term or preterm labor. The state of the cervix is commonly used as a predictor of labor. However, the dilatation of the cervix usually occurs relatively late, during actual labor. In addition, labor and changes in the cervix can occur independently. Alternatively the frequency of contractions is used to diagnose labor, sometimes recorded with a tocodynamometer. However, these methods give only crude subjective estimates of uterine contractility.

The uterus does not contract vigorously throughout most of pregnancy and this provides a tranquil environment for the growing fetus. At term, the uterus normally begins to contract forcefully in a phasic manner (labor) to expel the fetus. Contractions of the uterus are directly proportional to the underlying electrical activity of the muscle. The frequency, duration, and magnitude of a uterine contraction are directly proportional, respectively, to frequency of bursts of action potentials, and the propagation (also referred to as conduction) of action potentials over the uterus and the recruitment of muscle cells. A similar situation exists in heart muscle, although heart and uterine muscle are different with respect to structure and configuration of the action potentials. The action potentials are accompanied by the influx of calcium into the muscle cells to activate the contractile apparatus.

Thus, by recording uterine electrical activity one can assess the contractility of the myometrium. Similar technology is used to record cardiac electrical activity to determine the normal or abnormal function of the heart.

Many studies have previously recorded myometrial electrical activity using electromyography (EMG) where electrodes are placed directly on the uterus. These studies show that the myometrium generates little electrical activity prior to labor but activity increases tremendously during labor reflecting the mechanical events. Studies of interest are demonstrated in publications by Csapo, Chapter 43, "Force of Labor," *Principles and Practice of Obstetrics and Perinatology*, Ed. L. Iffy and H. A. Kaminetzky, John Wiley and Sons Publishing 761–799, 1981; Garfield et al., "Control of Myometrial Contractility: Role and Regulation of Gap Junctions," Oxford Rev. Reprod. Biol. 10:436–490, 1988; Wolfs and Van Leeuwen, "Electromyography observations on the human uterus during labor," Acta Obstet. Gynecol. Scand. [Suppl.] 90:1–62, 1979; and more recently by Devedeux et al., "Uterine Electromyography: A Critical Review," Am J. Obstet. Gynecol. 169:1636–1653, 1993. One may measure and use uterine EMG activity by direct contact with the uterus to predict normal and abnormal uterine contractions. However, it is not practical to place electrodes directly on the uterus. To do this under the present level of understanding one must surgically implant electrodes on the uterine surface or introduce a catheter electrode through the vaginal canal and puncture the fetal membranes.

It would be desirable to record uterine EMG activity from the abdominal, cervical or vaginal surface. Previous studies of electrical activity of the uterus recorded with electrodes placed on the abdominal surface failed to record bursts of action potentials from the uterus and generally showed no association of uterine electrical activity with contractility. Studies of interest are included in the above-noted publications by Wolfs and Van Leeuwea and by Devedeux et al. Wolfs and Van Leeuwea summarized all studies prior to 1979 and concluded, "it has never been clearly shown that the potential fluctuations obtained by means of electrodes attached to the abdominal wall, do indeed represent the electrical activity of the uterus." (Page 7.) Similarly, Devedeux et al state that abdominal monitoring of uterine electrical activity "requires further investigation" (Page 1649).

Recently, studies have been done which establish that there is significant correlation between the potentials of the uterus as measured at the abdominal surface and directly at the uterus. These studies show that such electrical signals can be quantified by mathematical means, for example, with Fourier analysis or Wavelet analysis: Garfield, R E, et al, "Control and assessment of the uterus and cervix during pregnancy and labour, 1996"; Buhimschi C, Garfield R E. "Uterine activity during pregnancy and labor assessed by simultaneous recordings from the myometrium and abdominal surface in the rat," Am. J. Obstet Gynecol 1998, 178:811-22; and Garfield R E, et al, "Instrumentation for the diagnosis of term and preterm labour," J. Perinat Med 1998; 26; 413–436.

Part of the difficulty in interpretation of electrical activity recorded from the uterus lies in the fact many investigators, including Wolfs and Van Leeuwea and Devedeux et al., have failed to recognize that action potentials drive the uterus to contract. Action potentials are not responsible for contraction of some smooth muscle tissues such as airway muscle and some vascular muscles, and therefore many researchers confound the uterus with other smooth muscles. Thus, many of these studies have attempted to correlate electrical activity with mechanical contractions in order to show that electrical activity is or is not responsible for contractions. It is now clear (from publications by Marshall, "Regulation of Activity in Uterine Smooth Muscle," Physiol. Rev. 42-212-

227, 1962; Csapo, Chapter 43. "Force of Labor," *Principles and Practice of Obstetrics and Perinatology*, Ed. by I. Iffy and H. A. Kaminetsky, John Wiley & Sons Publishing, 761–799, 1981; Garfield et al., "Control of Myometrial Contractility: Role and Regulation of Gap Junctions," Oxford Rev. Reprod. Biol. 10:436–490, 1988; and Garfield, Chapter 3 "Role of cell-to-cell Coupling in Control of Myometrial Contractility and Labor," *Control of Uterine Contractility*, Ed. R. E. Garfield and T. Tabb, CRC Press. 39–81. 1994) that action potentials activate the uterus to contract and that by measuring uterine electrical activity one can indirectly estimate contractility.

There has been much progress in monitoring adult ECG using an array of surface electrodes placed on the skin (*Interventional Electrophysiology*, $2^{nd}$ Edition, Ed. by Singer. Lippincott Williams & Wilkins, April 2002). There has also been some success in monitoring maternal and fetal cardiac activity from the abdominal surface of pregnant patients using electrodes (Kanjilal, et. al., "Fetal ECG Extraction from Single-Channel Maternal ECG Using Singular Value Decomposition," IEEE Trans Biomed Eng. January; 44(1): 51–9, 1997; Kwon, et. al., "Abdominal Fetal EKG Noise Removal," Biomed Sci Instrum. 32: 87–92, 1996). However, the devices and methods of data acquisition and signal processing delineated in these studies seem inadequate for proper patient evaluation and diagnosis.

In trans-abdominal recording of uterine EMG, maternal and fetal ECG, and fetal EEG, background noise due to respiration, patient movement and skin potentials is very high in about 15% of the records. What is needed is a system that is effective in non-invasively recording, identifying, and analyzing uterine EMG and/or maternal and/or fetal cardiac or fetal brain signals, simultaneously or separately, while reducing the effects due to background noise, in more than 95% of all pregnant patients.

SUMMARY OF THE INVENTION

The present invention presents a method and apparatus for recording and analyzing uterine electrical activity from the surface of the abdomen, vagina, or cervix for the purpose of diagnosing contractile patterns of the uterus in pregnant and non-pregnant patients, as well as monitor maternal and fetal ECG and fetal brain activity. The present invention provides data analysis techniques for analyzing the electrical data measured from the surface of a patient to characterize uterine, abdominal, and cardiac muscle activity of the patient, as well as cardiac and brain activity of the fetus simultaneously or separately.

The signals will be amplified and analog filtered for background noise. Possible filtering setups are to band-pass filter from about 0.001 Hz to about 3.000 Hz for uterine EMG or to filter from about 0.5 Hz to about 100 Hz for fetal EEG or to filter from about 1 Hz to about 5 Hz for fetal heart rate. Other filtering schemes can be used when certain uterine EMG and maternal fetal biophysical signal frequencies need to be isolated.

Additional filtering of background noise will be done by cross-correlation, auto-correlation, adaptive filtering, matched filtering, and/or singular value decomposition or other multi-channel methods, where common components of noise from any or all of the potentials recorded are reduced or removed, leaving the desired uterine EMG, maternal cardiac, and fetal brain electrical signals. The unit will have the capability of determining and/or modifying or maintaining phase relationships between various channel combinations in order to carry out such noise-reduction utilizing these methods.

In particular, the present invention contemplates a method of analyzing surface electrical data to characterize maternal uterine, maternal abdominal, maternal and fetal cardiac, and/or fetal brain activity, comprising applying a multi-polar arrangement of action potential-, or electrical signal-measuring electrodes to an abdominal, vaginal, or cervical surface of a patient; measuring electrical signals produced at the electrodes; analyzing frequency components of the electrical signals; and characterizing uterine, abdominal, cardiac or fetal brain activity of the patient based on the analysis of frequency components or other signal quantities. Ideally, the analysis of uterine activity indicating parameters is performed for data from at least three (3) bursts of action potentials within the stored electromyographic signals, and at least 30 minutes of recording for the electrical signals generally. The uterine burst analysis, or cardiac or brain signal analysis may include determining the frequency, duration, amplitude, number of action potentials per burst, activity per unit time of interest, and power density spectrum of at least three (3) bursts of action potentials and the frequency, duration, and amplitude of a plurality of action potentials or use of integration of signals, 3-dimensional mesh plots, vector analysis, wavelet transforms, power spectrum, Fourier transforms, spectral-temporal mapping, complexity, chaos, fractals, zero-crossings, randomness, non-linearity, likelihood ratios, and statistical methods, Wigner-Ville or Heisenberg-Gabor analysis (as would be known to those with ordinary skill in the art), or other joint time-frequency analysis for one or more of the uterine, cardiac, or brain signals. As a further embodiment, the method also includes predicting treatment for the patient based on the characterization of uterine, cardiac or fetal brain activity, in particular this treatment may be pharmacologically inducing or inhibiting labor in the patient.

The burst of action potentials may be analyzed using wavelet or Cepstrum Analysis, as described in Akay, Chapter 6, "Cepstrum Analysis," Biomedical Signal Processing, Academic Press (1994). The uterine, cardiac, and fetal brain signals may also be analyzed using non-linear dynamics, or chaotic analysis, as described in Molnar, et al., "Correlation Dimension of Changes Accompanying the Occurrence of the Mismatch Negativity and the P3 Event—Related Potential Component," Electroencephalography and Clinical Neurophysiology, 95 (1995), pp. 118–26; Elbert, et al., "Chaos and Physiology: Deterministic Chaos in Excitable Cell Assemblies," Physiology Reviews, Vol. 74, No. 1, Jan. 19, 1994; and Skinner, et al. "The Point Correlation Dimension Performance with Non-Stationary Surrogate Data and Noise," Integrative Physiological and Behavior Science, Vol. 28, No. 3, pp. 217–34 (September 1994). The uterine, cardiac, and fetal brain signals may also be analyzed using indices, comprising power density spectrum and frequency data. The distribution of intervals between successive action potentials may be characterized as an indicator of aberrant activity.

The invention also contemplates the stimulation of the vagina of the patient while the uterine electromyographic and maternal and fetal cardiac and fetal brain electrical signals are being stored. This stimulation permits the assessment from the stored electrical signals for the phenomenon of conduction, and permits the diagnosis of labor as a function of the signals, as well as an evaluation of maternal and fetal well-being based on cardiac and brain signals. The stimulation of the vagina may either be electrical, mechanical or pharmacological, for example through the infusion of oxytocin to the patient.

Other further embodiments contemplate isolating high frequency uterine electrical components within the electromyographic signals; isolating a fast wave component within the high frequency components; determining a low-frequency domain, including low-frequency components within the fast wave component, and a high-frequency domain, including high-frequency components within the fast wave component; and determining a relationship between the low-frequency domain and the high-frequency domain indicative of an obstetrical diagnosis. This relationship can be indicative of pre-term or term uterine activity.

Other embodiments of the present invention contemplate analyzing the uterine, cardiac, and fetal brain electrical frequency ranges of interest using wavelet analysis methods to de-correlate the signals, displaying the signal components by sub-band, and comparing the energy levels contained in particular sub-bands versus time of pregnancy. The wavelet transform or wavelet packet analysis may be used to generate various measures (such as amplitudes and ratios) of the wavelet maxima, skeleton, or energy content within particular sub-bands. The resulting decomposition(s) of the signal may be used in de-noising by thresholding, wavelet shrinkage, and comparable approaches. The signals may be compressed with high efficiency before storage by discarding the smallest wavelet coefficients.

An alternative embodiment of the present invention contemplates a method of analyzing transabdominal/transvaginal/transcervical uterine data to characterize the activity in the tissue, comprising applying an arrangement of multiple (tri-polar, quadra-polar, or other multi-polar configuration) action potential-, or electrical signal-measuring electrodes to a surface of a patient; measuring uterine, cardiac, and fetal brain signals picked up by the electrodes; analyzing the signals; determining potential vector characteristics of the signals to identify direction and rate of propagation of uterine electrical activity; and characterizing uterine activity based on the potential vector characteristics. This potential vector can be indicative of an obstetrical diagnosis, including pre-term or abnormal term uterine activity.

The apparatus of the present invention works in real-time and includes at least three electrodes (tri-polar, quadra-polar, etc. configurations) that are applicable to the abdominal, cervical or vaginal surface of the patient under analysis; differential analog filters/amplifiers electrically coupled to the electrodes and approved for human use, to receive and amplify a signal indicative of action potentials measured by the electrodes; an analog filtering device capable of segregating and identifying uterine, maternal and fetal cardiac, and fetal brain electrical signals, including action potentials, in pre-selected frequency ranges; an analog-to-digital converter, possibly incorporated into a digitizer, that is electrically coupled to receive an analog input from the amplifier indicative of action potentials, or electrical signals, measured by the electrodes, and that converts these electrical signals picked up by the electrodes into digitized data which are indicative of uterine, maternal and fetal cardiac, and fetal brain electrical signals; a program or hardware for combining multiple potentials or summing or performing various mathematical pre-processing of signals to yield the desired number and type of differential signals, each of which corresponds to a "channel" of the data acquisition system; a process for further reducing noise components common to one or more channels of data by utilizing a multi-channel process for noise elimination, such as auto-correlation, cross-correlation, adaptive filtering, matched filtering, and/or singular value decomposition, or any other such techniques; the capability of determining and/or modifying or maintaining phase relationships between various channel combinations in order to carry out such noise-reduction utilizing such methods; a memory for storing the digitized signals, and comprising sufficient storage capacity to store data resulting from a sampling of electromyographic signals at a sampling frequency of at least 100 Hz. for a duration of time sufficient to record on all channels for at least three (3) bursts of action potentials or 30 minutes, whichever is longer; and a programmed computer. The computer comprises an expert system programmed to generate and/or analyze the frequency, duration, amplitude, power density spectrum, integration of signals, 3-dimensional mesh plots, vector analysis, wavelet transforms, power spectrum, Fourier transforms, spectral-temporal mapping, complexity, chaos, fractals, zero-crossings, randomness, non-linearity, likelihood ratios, and statistical methods of the action potential bursts, trains, or groups, as well as individual action potentials of uterine, cardiac and fetal brain activity. The expert system is further capable of characterizing uterine, cardiac and fetal brain activity and of identifying abdominal muscle contractions, based upon this analysis or other analyses.

The expert system may comprise algorithms needed to perform a Cepstrum analysis, wavelet analysis, chaotic analysis, or myometrial analysis of the action potentials. The expert system may also be capable of identifying abdominal muscle contraction, and/or identifying and analyzing QRS complexes and heart-rate in maternal and fetal cardiac activity, determining alpha, beta, theta, and delta brain waves and their morphologies from the fetal brain electrical signals. The expert system may also be capable of evaluating the trend of uterine activity over the course of labor, encompassing many hours, to determine whether labor is progressing, and alerting the physician to the possible diagnosis of failure-to-progress and the need to treat by pharmacological, surgical, or electrical means. The expert system may be capable of assessing other clinical data in combination with the EMG data, such as the normality or abnormality of the maternal and fetal heart activity and fetal brain activity.

An alternative embodiment contemplated by the present invention is an apparatus for recording and analyzing uterine, cardiac, and fetal brain electrical activity from the abdominal surface, comprising at least three (3) action potential-measuring electrodes for recording electrical signals applicable to an abdominal surface of a patient under analysis; an analog-to-digital converter, connected to at least three electrodes, for converting electrical signals produced by the electrodes into digitized data indicative of the electrical signals; a memory for storing the digitized signals; and a programmed computer for analyzing frequency components of the stored digitized electrical signals, and for providing an indication of uterine, cardiac, and fetal brain electrical activity from the patient and the fetus under analysis as a function of the stored digitized signals. A still further embodiment contemplates an apparatus wherein the programmed computer is used further for determining power density spectral characteristics of the frequency components of the electrical signals.

The present invention further contemplates an apparatus in the form of a remote uterine monitoring system for analyzing surface electrical data to characterize uterine activity, maternal and fetal cardiac and fetal brain activity, comprising a remote uterine monitor and a central programmed computer in communication with the remote uterine monitor for analyzing stored digitized electrical signals, and for providing an indication of uterine, maternal and fetal cardiac, and fetal brain electrical activity from the patient and the fetus under analysis as a function of the stored digitized signals. The remote uterine monitor includes an arrangement of at least three (tri-polar, or quadra-polar, etc. configurations) action potential-, or electrical signal-measuring electrodes applicable to an abdominal surface of a patient under analysis; and a remote analog-to-digital converter, connected to the at least three electrodes, for converting electrical signals picked up by the electrodes into digitized data indicative of the uterine, maternal and fetal cardiac and fetal brain signals.

In a further embodiment, the remote uterine, cardiac, and fetal brain monitor and the central programmed computer communicate on-line through a telephone line or through wireless communication, such as digital or cellular phones or over radio or television frequencies, for example. In a still further embodiment, the remote uterine monitoring system also includes remote signal processing, analysis, and storage for recording the digitized electrical signal data, and wherein the central programmed computer communicates with the remote uterine monitor off-line through the remote storage device (for example, through Bluetooth or similar technology). In a still further embodiment, the remote uterine monitoring system communicates to pagers and/or cellphones directly on the person of the doctors or hospital staff involved in treating/monitoring the patient and the fetus in question, or to family members of the patient in question, etc.

A method is provided for characterizing uterine electrical activity, comprising applying an action potential measuring multi-polar arrangement of electrodes to an abdominal, vaginal or cervical surface of a patient; isolating a system from the patient for analog filtering and amplifying an electrical signal as appropriate to isolate desired frequency components of said signal from background noise in said signal; acquiring analog electrical uterine, maternal or fetal cardiac signals, fetal brain signals, or a combination thereof transmitted through said electrodes at a sampling frequency between about 0.5 and 1 kHz for a duration of time sufficient to record at least 3 bursts of action electrical potentials from said signals; removing unwanted signal components through a multi-channel noise elimination scheme; storing said acquired signals; using detection algorithms to detect one or more attributes of said uterine, maternal or fetal cardiac activity, fetal brain activity, or combination thereof that are present in said acquired signals; analyzing at least a portion of said activity, indicating parameters from at least one burst of the action potentials within the stored signals; characterizing said activity from said patient based on said parameter analysis; determining electrically when contractions occur and plotting the contractions; simulating data output of a tocodynamometer or an intra-uterine pressure catheter; and predicting when a patient will go into labor or delivery, or a combination thereof.

Further, a system is provided for recording and analyzing uterine electrical activity for the abdominal, cervical or vaginal surface, comprising: an arrangement of at least three electrodes forming a multi-polar arrangement adapted to measure electrical signals due to action potentials emitted from an abdominal, vaginal, or cervical surface of a patient under analysis to establish uterine, maternal and fetal cardiac, and fetal brain signals and each electrode further adapted to conduct an analog signal indicative of said action potentials, each electrode-pair being identified with one channel of data; at least one analog filter adapted to remove unwanted signal components from the uterine, maternal and fetal cardiac, and fetal brain signals; at least one differential, isolated, analog amplifier electrically coupled to said electrodes to receive and amplify signals indicative of said action potentials measured by said electrodes; at least one analog to digital converter adapted to generate digital signals from the analog signals produced by the amplifiers; at least one memory comprising sufficient storage capacity to store data resulting from a sampling of electrical signals at a sampling frequency of at least 100 Hz from a single patient for at least 1 hour, said memory adapted to receive a digital input from said analog to digital converter; a computer programmed to import electrical signal data from multiple channels, or multiple differential signals from multiple electrode-pairs, formed from an array of said multi-polar arrangement of electrodes, and to perform mathematical functions on at least two of the potentials measured to generate multiple channels of data which are the result of at least one mathematical combination of said potentials from said mathematical functions; said computer programmed to perform multi-channel filtering on at least one of the channels of data to remove unwanted noise components common to one or more channels; said computer programmed to analyze frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis on the uterine, cardiac, and brain signals acquired, said computer further being adapted to characterize uterine, maternal and fetal cardiac, and fetal brain activity based upon said analysis. Further, the system can be used to plot contractions, plot contraction strength, assess maternal and fetal heart activity, and fetal brain activity, and accurately predict labor and delivery, without the need for using a tocodynamometer or an intra-uterine pressure catheter, or other such typical devices.

In another embodiment, a remote uterine monitoring system is provided for remotely characterizing uterine activity, comprising: at least three electrodes forming a multi-polar arrangement adapted to measure electrical signals of action potentials emitted from an abdominal, vaginal, or cervical surface of a patient under analysis and further adapted to emit an analog signal indicative of action potentials measured by said electrodes; an isolation system comprising analog filters adapted to remove unwanted signal components from the uterine, maternal and fetal cardiac, and fetal brain signals; at least one analog differential amplifier coupled to said electrodes, isolated from the patient by said isolation system, and adapted to receive and amplify signals indicative of action potentials measured by said electrodes; a computer programmed to import electrical signal data from multiple channels, or multiple differential signals from multiple electrode-pairs, formed from an array of said multi-polar arrangement of electrodes, and to perform mathematical functions on two or more of the channels to generate channels of data, which are the result of such mathematical combination of said potentials; said computer adapted to perform multi-channel filtering on said channels of data to remove unwanted noise components common to one or more channels; said computer programmed to analyze the frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis on the uterine, cardiac, and brain signals acquired, said expert system further being adapted to characterize maternal uterine, maternal and fetal cardiac, and fetal brain activity based upon said analysis; at least one data transmission system, coupled to said computer, adapted to transmit uterine, maternal and fetal cardiac, and fetal brain signals, processed or unprocessed, to a remote location from said computer via a telecommunications link; at least one remote analog to digital converter coupled to said data transmission system to receive an analog input from said amplifier indicative of action potentials measured by said electrodes; at least one memory comprising sufficient storage capacity to store data resulting from a sampling of trans-abdominal, trans-vaginal, trans-cervical electrical signals, or a combination thereof, at a sampling frequency of at least 100 Hz from a single patient for at least 1 hour, said memory adapted to receive a digital input from said analog to digital converter indicative of action potential signals received by said converter; at least one receiver adapted to collect the uterine, cardiac, or brain data, processed or unprocessed, which is transmitted from said computer at the site of the patient; and at least one remote computer located remote from the patient and coupled to said receiver to import received data from the site of the patient and programmed to analyze the frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis on the uterine, cardiac, and brain signals acquired, said remote computer further being capable of characterizing maternal uterine, maternal and fetal cardiac, and fetal brain activity based upon said analysis.

These and other features and advantages of the present invention will become apparent to those of ordinary skill in this technology with reference to the following detailed description and appended drawings.

BRIEF DESCRIPTION OF THE DRAWINGS

A more particular description of the invention, briefly summarized above, may be realized by reference to the embodiments thereof that are illustrated in the appended drawings and described herein. However, it is to be noted that the appended drawings illustrate only some embodiments of the invention. Therefore, the drawings are not to be considered limiting of its scope, for the invention may admit to other equally effective embodiments.

Various features and attendant advantages of the present invention will be more fully appreciated as the invention becomes better understood when considered in conjunction with the accompanying drawings, in which like referenced characters designate the same or similar parts throughout the several views, and wherein.

DETAILED DESCRIPTION OF THE INVENTION

Any one or more of the following numbered functions, steps, blocks, or components of the present invention may be included or excluded at any time during the design or construction of, or during the use of the instrument by the designer, builder, or operator, as desired, and each function or component of the present invention delineated below is optionally included in the present invention or used by the operator of the present invention.

Figure 1:
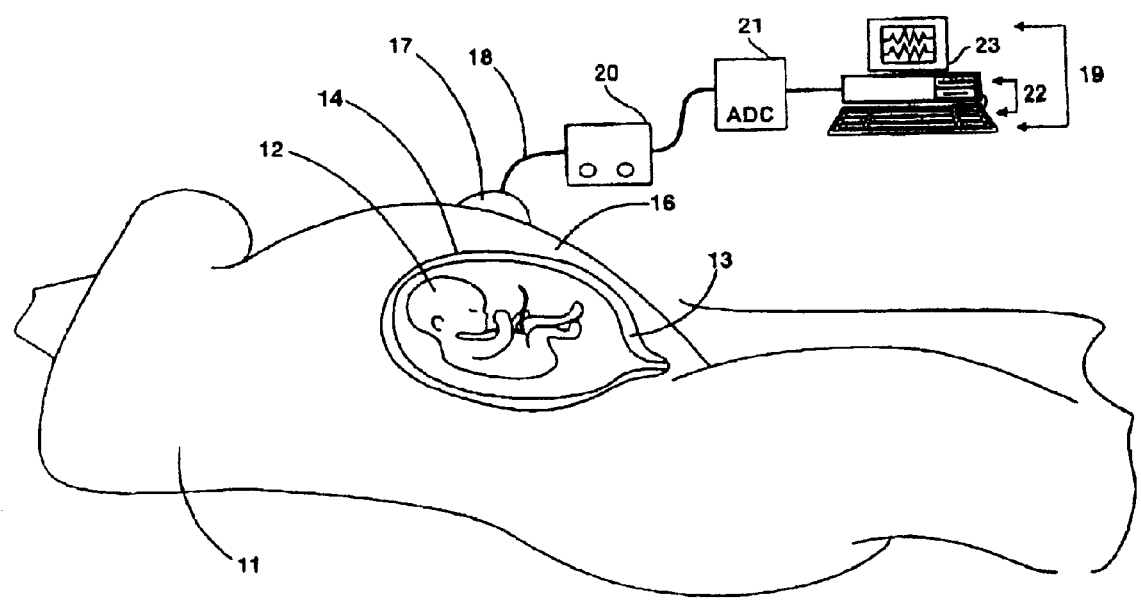
FIG. 1 is a schematic side view showing the recording apparatus in accordance to the present invention attached to the abdominal surface of a pregnant patient with an interior view of a fetus in the uterus.

FIG. 1 is a schematic side view showing the recording apparatus in accordance to the present invention attached to the abdominal surface of a pregnant patient with an interior view of a fetus in the uterus. FIG. 1 shows schematically a pregnant patient 11 with a fetus 12 retained within the uterus 13. The uterine wall 14 is primarily configured of muscle tissue and is disposed proximate to the abdominal wall 16 of the patient 11. In accordance with the principles of the present invention, advantageously a tri-polar, quadra-polar, or other multi-polar arrangement of electrodes 17 are placed on the exterior of the patient 11 on the abdominal wall 16. In another embodiment, electrodes 17 may be placed on the vaginal or cervical surface of the patient. The electrodes 17 have leads 18 that are connected to a recording apparatus 19 including isolated (electrically, optically, etc.) analog filters/amplifiers 20, analog-to-digital converter (ADC) 21, computer 22 and monitor 23. In a preferred embodiment, potentials measured at the electrodes, whether made respect to a ground lead, or measured directly, are summed, averaged, converted to absolute values, or otherwise combined or manipulated with hardware/software prior to receipt at the filters of filters/amplifiers 20. In another preferred embodiment, potentials measured at the electrodes, whether made respect to a ground lead, or measured directly, are summed, averaged, converted to absolute value, or otherwise combined or manipulated with hardware/software after passing through the filters of filters/amplifiers 20, but before amplification. In another embodiment of the present invention, similar combination or manipulation of various potentials or channels could be made alternatively after the amplification stage in filters/amplifiers 20.

In a preferred embodiment, isolated analog filters/amplifiers 20 are used to amplify the signals received from electrodes 17 after filtering the analog signal for the desired application, whether uterine, maternal and fetal cardiac, or fetal brain activity or a combination of one or more of these. The unit will be isolated from the patient and approved for use in human patients. The ADC, computer and monitor may be replaced or augmented by other output indicators, such as chart recorders or indicator lamps or audio monitors. The ADC could be incorporated into a digitizer.

In accordance with the principles of the present invention, the uterus 13, and maternal and fetal heart and fetal brain of the pregnant patient 11 are monitored for electrical activity from signals (sometimes referred to herein as "uterine, maternal and fetal cardiac and fetal brain" signals) detected on the surface of the abdomen, or alternatively from the vaginal or cervical surface via a multi-polar arrangement of electrodes. In a preferred embodiment, the uterine, maternal and fetal cardiac, and fetal brain signals are analog filtered to eliminate unwanted noise and perhaps further filtered using a multi-channel filtering scheme, such as cross-correlation, auto-correlation, matched filtering, adaptive filtering, and/or singular value decomposition or other such techniques. The machine will utilize the capability of determining and/or modifying or maintaining phase relationships between various channel combinations in order to carry out such noise-reduction using such methods. The signals are then amplified by filters/amplifiers 20, digitized by ADC 21, and displayed on a monitor 23. In an alternative embodiment, multi-channel filtering to remove noise components common to one or more channels would be accomplished alternatively after amplification in 20. The signals are also stored in the memory 24 of computer 22 for analysis of the frequency duration and other characteristics of the action potentials.

Figure 2:
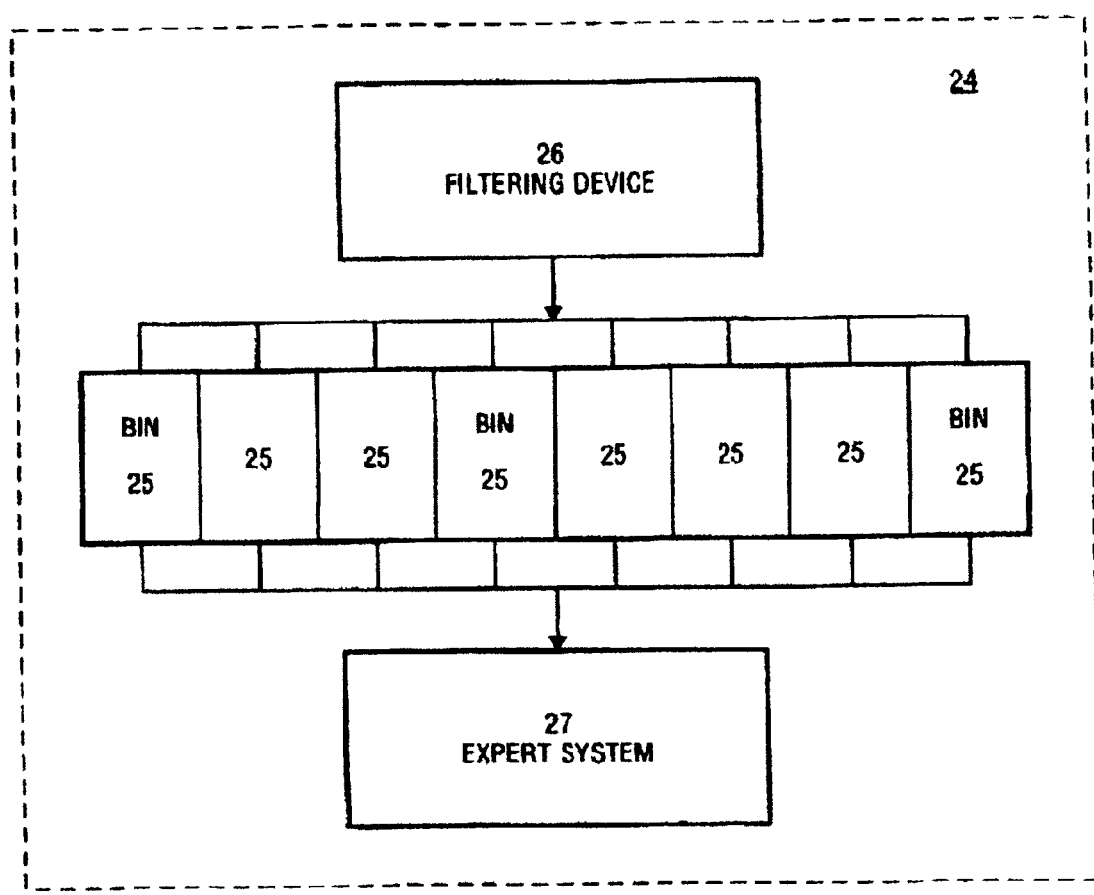
FIG. 2 is a schematic block diagram of signal filtering, memory, and expert system of the present invention.

FIG. 2 is a schematic block diagram of signal filtering, memory, and expert system of the present invention in one embodiment. The separation of signal frequency components into bins with hardware is optional. The process could also be done in software or firmware. A memory 24 comprises an optional filtering hardware device 26 capable of segregating and identifying uterine, maternal and fetal cardiac, and fetal brain signals including action potentials in predetermined frequency ranges, an optional multiplicity of bins 25 for storing electrical signals in discrete predetermined frequency ranges, and expert system 27 programmed to analyze the frequency, duration, amplitude and power density spectrum of action potential bursts and individual action potentials and further capable of characterizing uterine activity and identifying muscle contractions, based upon such analysis. In an alternative embodiment, functions performed by filtering and bin devices 25 and 26 are carried out by software.

In a preferred embodiment, expert system 27 is also capable of determining the mean frequency, starting frequency, and ending frequency of a plurality of action potentials. In another preferred embodiment, the expert system 27 is also capable of identifying abdominal muscle contractions. In another preferred embodiment, the expert system 27 is also capable of evaluating long-term trends in uterine, maternal and fetal cardiac, and fetal brain activity as indicating the progression of labor. In another embodiment, the expert system may compare records from the same patient taken at different times during her pregnancy and predict the onset of labor at term. In another preferred embodiment, the expert system 27 is capable of using uterine, maternal and fetal cardiac and fetal brain data acquired by the present invention as well as using the data collected in combination with data acquired by other means to suggest possible diagnoses.

In a preferred embodiment, the present invention will be used to detect and plot contractions, by processing the uterine electrical signals, without the need for a tocodynamometer measurement of mechanical contraction activity. The preferred method of electrical signal processing will incorporate the use of changes in frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis to discern the changes of the uterine signal properties when contractions are present compared to quiescent periods when there is no contraction. The method employed will display vs. time a real-time or post-recording plot of the contraction activity, by plotting a relatively flat line when no contractions are present, and will plot a bell-shaped curve to indicate when contraction events take place. The peak of the bell-shaped curve will indicate where the parameter employed indicates the greatest change from the quiescent periods. The recording generated will be so indistinguishable from the plot generated by a tocodynamometer as to be read and interpreted by clinicians just as one reads and interprets a plot generated by a tocodynamometer. The clinical/diagnostic applications of the interpretation of this electrically generated contraction plot will be identical to the clinical/diagnostic applications of the interpretation of the typical tocodynamometer plot currently used in clinics. The ability to generate the contraction plots without the need for a tocodynamometer does not preclude the use of the present invention in combination with any and all other medical devices.

In a preferred embodiment, the present invention will be used to detect and plot contractions and display strength of contractions, by processing the uterine electrical signals, without the need for an intrauterine pressure catheter. The preferred method will incorporate the use of changes in frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis to discern the changes of the signal when contractions are present, and to assess from the electrical signals what the strength of the mechanical contraction activity is. Using this analyzed information, the quiescent periods and contractions as assessed by the processed electrical signals will be plotted real-time or post-recording as detailed in the previous embodiment, but additionally, the contraction activity plotted can be optionally scaled as is an intrauterine pressure catheter reading, and can be read, interpreted, and applied clinically as would an intrauterine pressure recording. The ability to generate the contraction plots and the corresponding strength of the contractions without the need for a intrauterine pressure catheter does not preclude the use of the present invention in combination with any and all other medical devices.

Returning to FIG. 1, and in accordance with one embodiment of the present invention, ADC 21 may be, for example, incorporated as a digitizer, such as the NI 5112 from National Instruments, Austin, Tex. Analog filters may be custom-made or commercial. Amplifiers/filters 20 may be, for example, BMA-931, complete with isolation head-stages ISO-Z, from CWE, Inc. Ardmore, Pa. Computer 22 with monitor 23 may be, for example, any IBM PC compatible computer, preferably with a Pentium 4-type (or better) microprocessor, one (1) Gigabyte of RAM, and a 20 Gigabyte hard drive and a super-VGA (or better) display, or an IBM lap-top computer, or any other equivalent computer and monitor. Computer 22 may also include several types of long-term storage devices, including recordable CD-ROM, tape, or high-capacity disks, such as "zip" or "jag," or other removable cartridges.

Although specific examples have been given for the various hardware components shown in FIGS. 1–2, it will be understood that different hardware components may be used, without departing from the spirit and scope of the present invention. As well, some of the functions given as hardware functions may also be delegated to software or firmware for performing them.

The collection of filters/amplifiers 20, used to process the two or more channels of signal input from the quadra-polar or other multi-polar arrangement of electrodes, whether preprocessed or not with filtering, summing, averaging, and/or absolute value functions (or other mathematical analog or digital preprocessing of signals), include controls for amplifying or attenuating the signals and also filters for elimination of some of the high or low frequency noise. The amplifiers are, for example, battery powered, or optically isolated, AC/DC differential amplifiers approved for use in human applications. The following non-limiting and approximate specifications, although other specifications can be used, are to be incorporated into the present invention:

Gain, AC and DC X100, X1,000 and/or X10,000 selectable

Input resistance: $10^{15}$ ohms

Leakage current: <50 pA typical

Common Mode Rejection:
>120 db:1 min @ 60 Hz

Noise, input shorted:
<1 $\mu$V p—p, 0.001 Hz-1 Hz

Low Freq filter settings:
0.001 Hz, 0.01 Hz, 0.1 Hz, 1.0 Hz, 3.0 Hz, 10 Hz, 20 Hz, 50 Hz, 100 Hz, 200 Hz, 300 Hz
selectable High Freq filter settings:
1.0, 3.0, 10 Hz, 20 Hz, 50 Hz, 100 Hz, 200 Hz, 300 Hz selectable Output resistance: 220 ohms Any combination of high and low frequency cutoffs shown using values listed above for band-pass filtering of signals can be selected on any filter/amplifier independently of any other settings on that or any other filter/amplifier, so that filtering/amplification can be controlled separately for each differential channel acquired. For example, one differential channel could optionally monitor EEG signals of a certain type, while another could monitor uterine action potentials, and so on. Other cutoff frequencies, as desired, for either high-pass or low-pass may be added as an option to those indicated above, or one or more of the optional settings indicated above may be changed or eliminated as needed in the design and/or use of the present invention.

It is important that the filters/amplifiers 20 be of sufficient quality and design to accommodate uterine, maternal and fetal cardiac, and fetal brain activity, simultaneously if desired, as measured from the surface of the abdomen, vagina, or cervix.

Estimates for normal values for the parameters for action potentials for human labor patients are presented in the following tables. (Note that these values are obtained when measuring potentials directly from the respective tissue. Amplitude values of these potentials acquired from the maternal abdominal surface, for example, may be 10 or more times weaker in some patients.)

| UTERINE ACTION POTENTIALS | |
|---|---|
| Frequency: | 0.01 Hz–1.2 Hz |
| Duration: | 50–200 milliseconds |
| Amplitude: | 0.2–1.2 millivolts |
| CARDIAC ACTION POTENTIALS | |
| Frequency: | 20 Hz–200 Hz |
| Duration: | >300 milliseconds |
| Amplitude: | 110–140 millivolts |
| FETAL BRAIN ACTION POTENTIALS | |
| Frequency: | 0.5 Hz–200 Hz typical |
| Duration: | From 1 millisecond to 2 seconds |
| Amplitude: | <5 microvolts |

In another embodiment, filters/amplifiers 20 may carry out several stages of signal processing and analysis, including action potential detection and power spectral analysis, by analog hardware implementations of algorithms, such as on a digital signal processing (DSP) board.

The computer 22 and monitor 23 may be of conventional PC design with software and hardware to digitize the signals as a preferred embodiment. The computer 22 is programmed with software to enable computer 22 to acquire, store, display and analyze the signals. This software may comprise an integrated general-purpose or customized software suite such as DataPac, LabView (National Instruments), Labwindows (National Instruments), Matlab (Mathsoft), or Benoit (Tru-soft). Additional software with extended signal-processing or statistical analysis capabilities may also be utilized, such as MatLab (The Math Works, Inc.) or S-Plus with S+ Wavelets (MathSoft). The operation of computer 22, in accordance with the present invention, is discussed below in detail with reference to the flow charts of FIGS. 4A–4E.

The analysis capabilities of the present invention are advantageously both real-time and predictive. In the real-time analysis, action potential parameters are analyzed in order to assess the present or real-time status of the patient's condition. In the predictive analysis, a series of action potential parameters are analyzed as a function of time in order to predict uterine contractility, based upon one or more identified trends of examined uterine activity indicating parameters.

Figure 3:
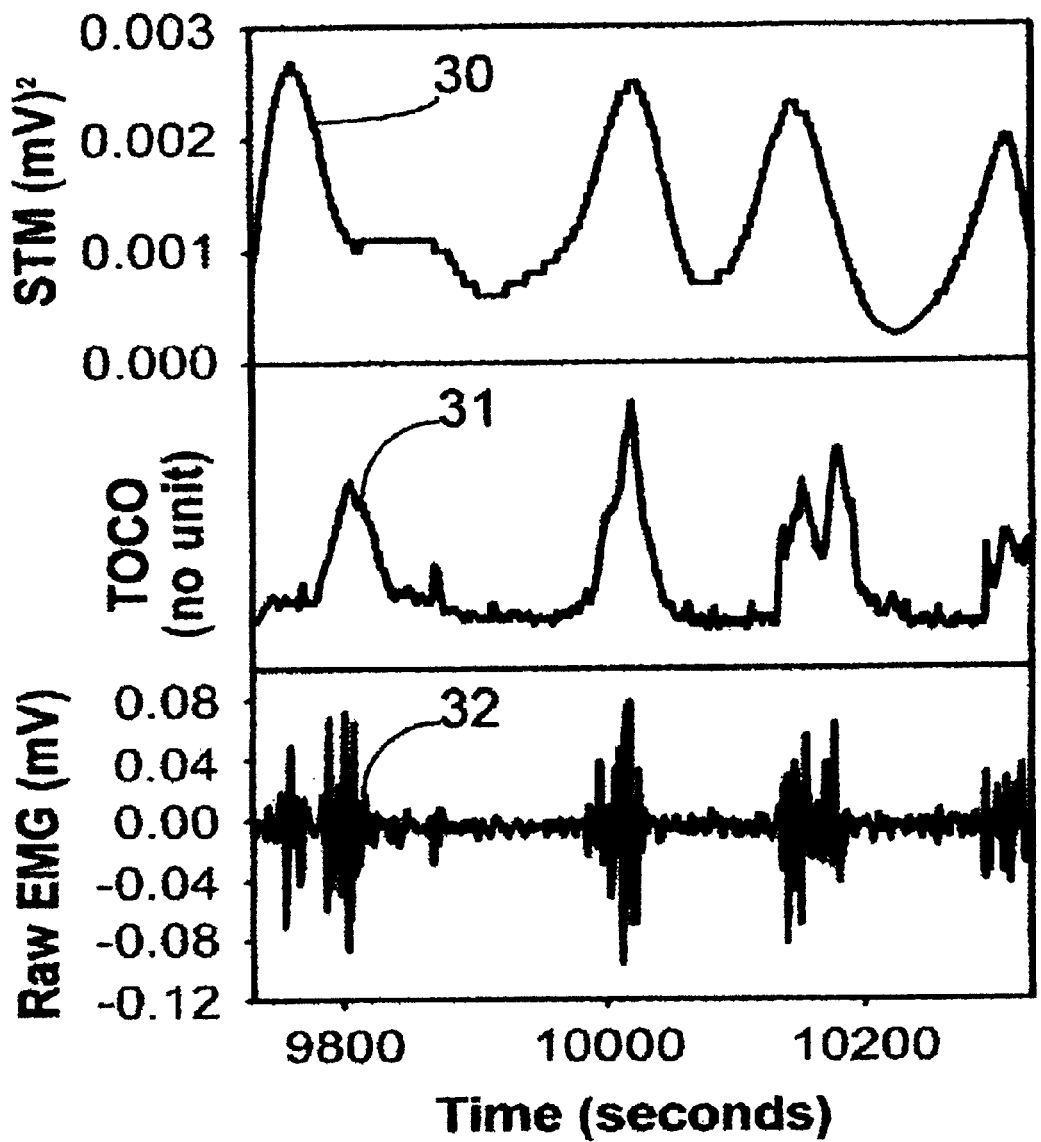
FIG. 3 is a schematic plot versus time of raw electromyography, tocodynamometry, and spectral-temporal mapping-processed electromyography signals as recorded from the abdominal surface of a pregnant patient.

FIG. 3 displays three plots: a plot (30), generated by processing trans-abdominal uterine EMG signals with spectral-temporal mapping as one method in accordance with the present invention; a simultaneously-recorded corresponding plot (31), generated by a standard tocodynamometer; and a plot (32), the raw EMG signal used to generate the processed EMG plot. The high degree of correspondence of plot 30 to plot 31 is grounds for using the present invention as a replacement to the tocodynamometer.

FIGS. 4A–4E are schematic flow charts of one method of the present invention. These figures depict the operation of the apparatus of FIGS. 1–2, in accordance with the present invention. In practice, the flow charts of FIGS. 4A–4E are embodied in a computer program or expert system used to control the operation of computer 22 of FIG. 1. The below discussion of the flow charts refer to reference numbers from FIGS. 1–2 where appropriate. Beginning in block 41 of FIG. 4A, computer 22 acquires trans-abdominal, trans-vaginal, or trans-cervical signals that are picked up by a multi-polar arrangement of electrodes 17, and which have been filtered and amplified by the isolated differential analog filters/amplifiers 20 and digitized by ADC 21. Also in block 41, either prior to or after analog filtering and/or amplification, mathematical functions in either hardware or software, and selected by the operator, are applied to the various channels of data to combine the potentials as desired, such as using summing, inverting, absolute values, or averaging or other functions to generate the desired number and type of superpositions or combinations of the original potential signals (details are given in the description of FIGS. 5A–5C below. Also in block 41, either prior to or after analog filtering and/or amplification, multi-channel filtering, such as cross-correlation, auto-correlation, matched filtering, adaptive filtering, and/or singular value decomposition or other such techniques is performed to further suppress remaining unwanted noise components common to one or more of the channels in question. The machine will have the capability of determining and/or modifying or maintaining phase relationships between various channel combinations in order to carry out such noise-reduction utilizing such methods. In block 42, digitized versions of the uterine, maternal and fetal cardiac and fetal brain signals are stored in the memory of computer 22.

Control then passes to block 43 where the stored uterine, maternal and fetal cardiac, and fetal brain data is analyzed to assess parameters reflecting groups, bursts, or tracings of uterine, cardiac, or brain action potentials present in the stored electrical signals. These analysis blocks are shown in more detail with reference to FIG. 4B. Control then passes to block 44 wherein the stored electrical signals are analyzed to determine parameters characterizing the individual action potentials within the stored uterine, maternal and fetal cardiac, and fetal brain signals. The details of the action potential analysis are shown in FIG. 4C.

Control then passes to block 46 where probability analysis is conducted on the electrical signals' characteristics determined in blocks 43 and 44. The details of this probability analysis are shown with reference to FIG. 4D.

Control then passes to decision block 47 where, based upon the probability analysis performed in block 46, it is determined whether the stored electrical signal reflects normal or abnormal uterine, maternal and fetal cardiac, and fetal brain function. The details of this diagnostic decision are shown below with reference to FIG. 4E.

If normal uterine function is concluded by decision block 47, and no abnormality is detected in maternal and fetal cardiac and fetal brain activity, control passes to one or more blocks 48A, 48B, and 48C. Blocks 48A, 48B, and 48C are collectively referred to as block 48. Likewise, blocks 49A, 49B, and 49C are collectively referred to as block 49. The normal uterine function is characterized (in block 48A) as non-labor, pre-labor or labor based upon characteristics of the bursts and action potentials as well as possibly patient clinical data. In a possible embodiment, predictions as to time of delivery and/or probabilities as to delivery or no delivery within various time-periods could also be displayed in block 48A. If uterine abnormality is concluded by decision block 47, control passes to block 49A where the abnormality is characterized as preterm labor, dystocia or other abnormalities based upon characteristics of abnormal bursts and action potentials as well as possibly patient clinical data.

If block 47 determines maternal and fetal cardiac is normal (block 48B) and fetal brain normal (block 48C), then the program may display an "OK" indicator for the respective physiological phenomena, or have no effect whatsoever on the program or system, or may simply have values displayed pertaining to the respective normal phenomena, etc. Maternal and fetal cardiac abnormalities block 49B) and fetal brain abnormalities (block 49C) detected could either trigger alarms or warnings, display the abnormal values, and/or could terminate the program or allow the program to enter another level of diagnostic calculations to analyze further the abnormal signals in question and give a detailed report on the problem encountered.

In a preferred embodiment, tracings that show no visible sign of uterine, and/or maternal and/or fetal cardiac and/or fetal brain electrical activity can still be acquired and analyzed by the present invention by treating sections of the traces or the entire recording of the traces as groups of individual action potentials. This is possible to do because there may often be uterine, cardiac, and/or brain electrical contributions to the recordings that are hidden from view of the naked eye, and would possibly be indiscernible from background noise upon first inspection. In this case, only inspection of the tracings using any one or more of the techniques in block 65 of FIG. 4C will be useful in detecting the appropriate biological activity and then for analyzing the signals and then for diagnosing patient and fetal conditions and/or predicting labor/delivery based on the analysis of said signals. Such will also be the case for quiescent or non-active periods between active periods in recordings for which there are discernible action potentials and/or groups or bursts of action potentials evident in the recording. The quiescent periods between the obvious or discernible activity or activities may still contain useful information and the present invention will be capable of analyzing these periods in the recordings as well as the more apparent activity, again by utilizing or evaluating one or more of the specified methods, techniques, or mathematical processes/procedures/parameters described in block 65, above.

Figure 4A:
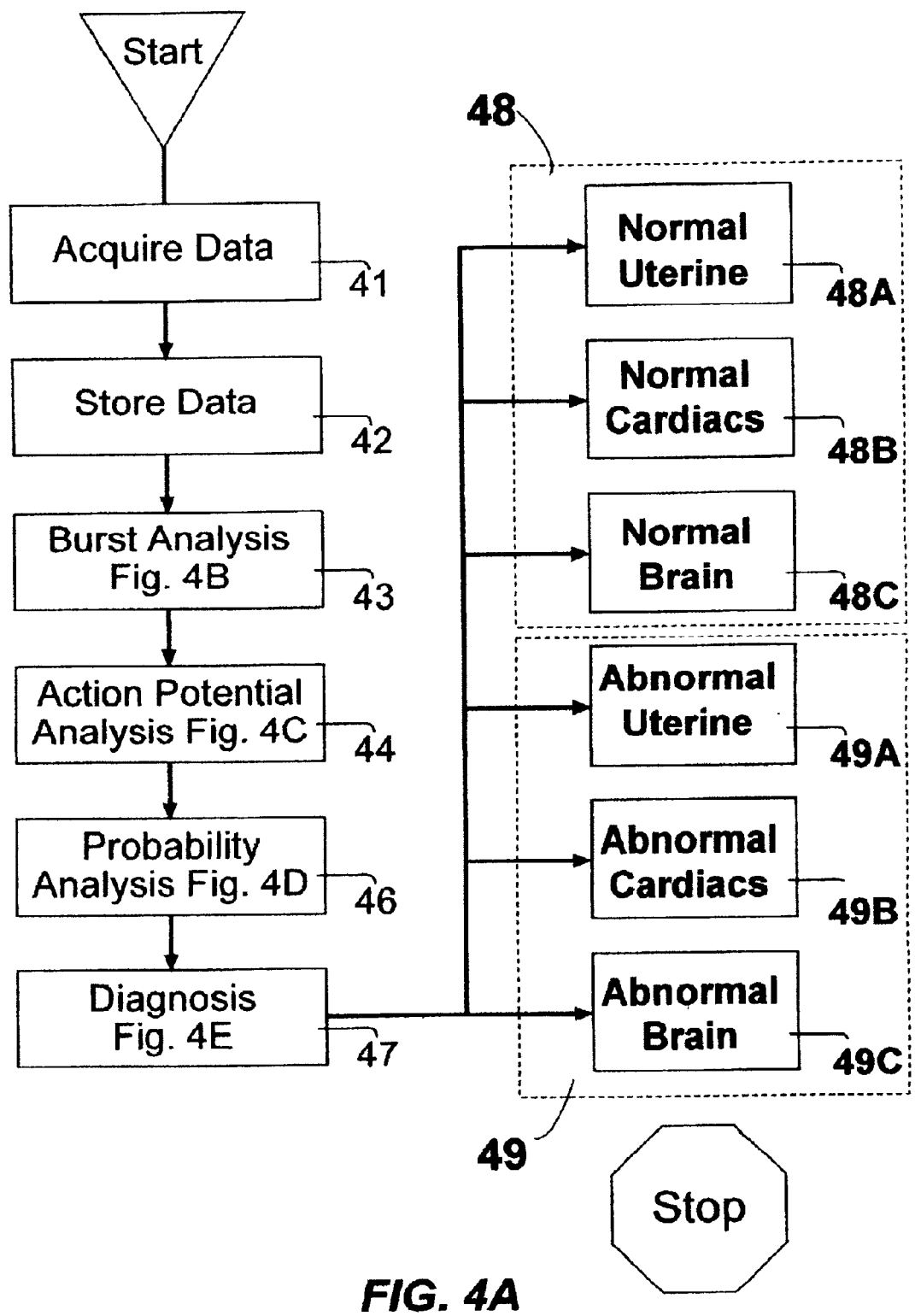
FIGS. 4A–4E are schematic flow charts of one method of the present invention.
Figure 4B:
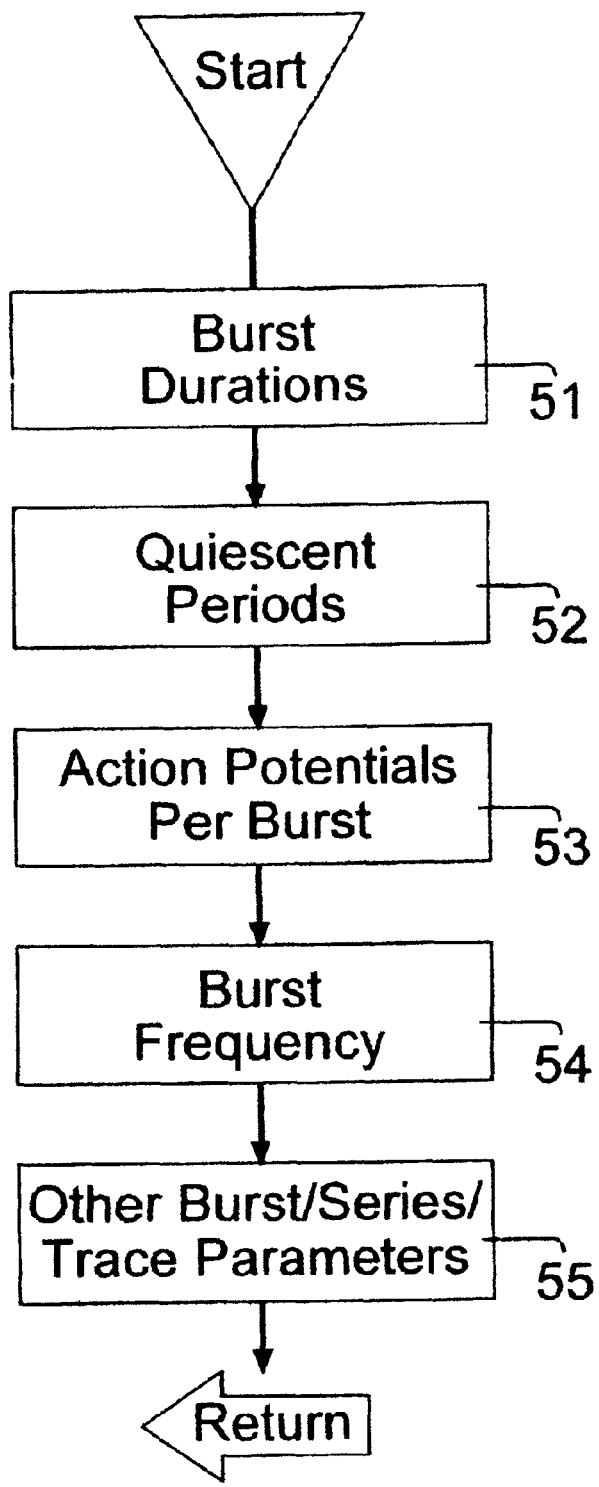
Figure 4C:
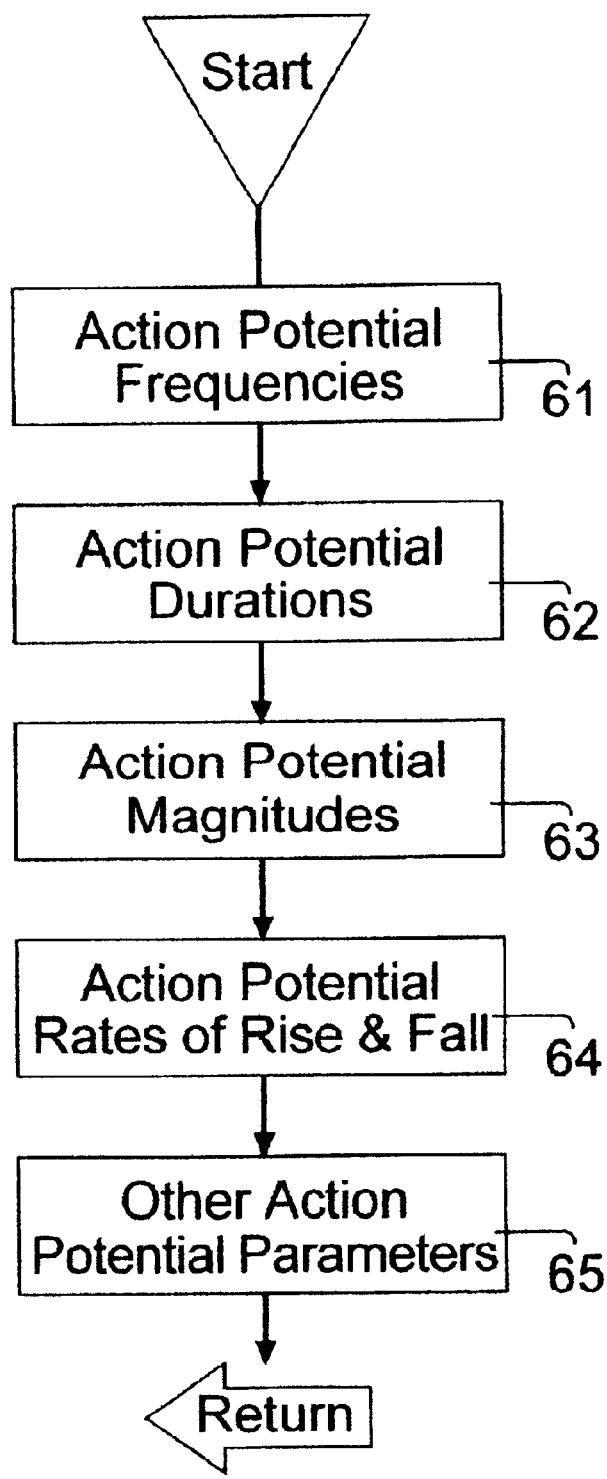

Referring now to FIG. 4B, the details of the analysis of uterine electrical bursts or series and maternal and fetal cardiac electrical bursts or series and fetal brain electrical bursts or series, conducted within block 43 of FIG. 4A, are presented.

Beginning, control passes to block 51 where the duration of each uterine, maternal and/or fetal cardiac, and/or fetal brain electrical burst (set of action potentials, each subsequent action potential being separated by a relatively short period of time from the previous action potential) or series (set of action potentials, each subsequent action potential being separated by a relatively long period of time from the previous action potential), each being known to those with ordinary skill in the art, is determined by measuring the time from the first action potential of the burst or series until the final action potential of the burst. Then, in block 52, the quiescent periods between the bursts are determined from measurements of the last action potential in a burst to the first action potentials in another burst. Then, in block 53, the number of action potentials in each uterine, cardiac and/or fetal brain electrical burst or series is determined. In block 54, the frequency of bursting is determined by estimating the number of bursts per unit time.

Again referring to FIG. 4B, the analysis of burst activity is conducted on uterine electromyographic signals stored from advantageously at least three (3) bursts of uterine action potentials. In block 55, any one or more of the following techniques may be applied to analyze the uterine, maternal and fetal cardiac, or fetal brain electrical bursts, groups, series of action potentials or traces of multiple action potentials: signal frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis. Control is then returned to the flow chart of FIG. 4A.

In FIG. 4B, maternal and fetal cardiac electrical activity may be analyzed (block 55) using one or more of the following: values of or changes in values of frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis applied to the electrical signals acquired to determine heart rates, QRST complexes, and other pertinent cardiac functions, while fetal brain activity may be analyzed (block 55) similarly to determine values for alpha, beta, theta, delta, and other important brain frequencies, as well as their morphologies, and possibly other fetal brain parameters.

FIG. 4C presents the details of the analysis of uterine, maternal and fetal cardiac and fetal brain action potentials performed by block 44 of FIG. 4A. Beginning in block 61, the frequencies, for example, of action potentials are determined by estimating the number of pertinent action potentials per unit time. Then, in block 62, the durations, for example, of the action potentials are determined by measuring the time from depolarization to repolarization. Control then passes to block 63 where the magnitudes, for example, of the action potentials are determined from measurements of the peak voltage of the depolarization. Control then passes to block 64 where the rates of rise of the action potentials, for example, are determined by determination of the slope dv/dt of depolarization. Conduction is estimated in a known manner from the rate of rise of action potentials. In general, the greater the rise-rate, the higher the conduction. Conduction may also be estimated from analysis of data when more than one surface electrode is used and time between action potentials from separate electrodes is estimated. In another preferred embodiment, the rate of all of the action potentials is also determined. The rate of fall is also useful in estimating conduction. In addition to frequency, duration, magnitude, and rate of rise and fall of the action potentials, in block 65, any one or more of the following may be applied to analyze uterine, maternal and fetal cardiac, or fetal brain electrical action potentials: frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis. Control then returns to the flow chart of FIG. 4A.

Figure 4D:
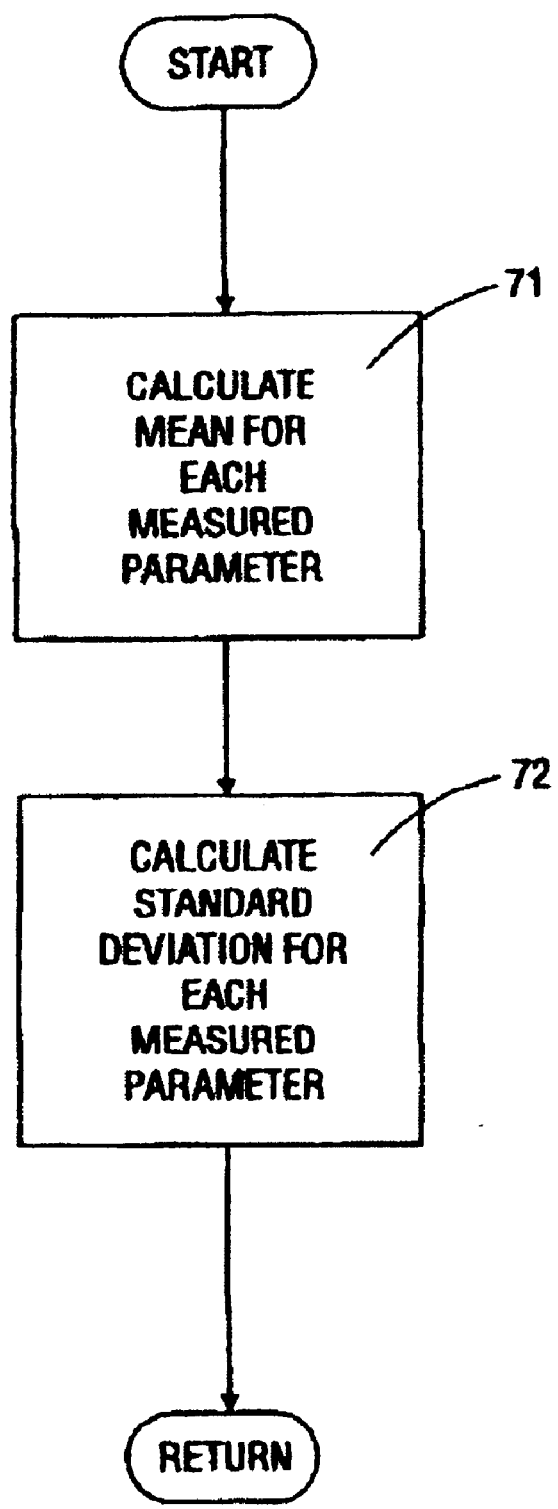

FIG. 4D shows details of the probability analysis performed by block 46 of FIG. 4A. Beginning in block 71, the mean of each of the measured parameters for bursts, groups of action potentials and/or traces of action potentials for the uterus, maternal and fetal cardiac and fetal brain is determined for each patient (see FIG. 4B), and then the same is done for the parameters of action potentials themselves (see FIG. 4C). Then, in block 72, the standard errors and standard deviations of each of the parameters for bursts/groups/traces and action potentials for the uterus, maternal and fetal cardiac and fetal brain are calculated. Other pertinent statistical parameters for comparison purposes later may also be made, as desired or required in this block. In a preferred embodiment, other properties of the distributions of these parameters are also considered, such as the positive and negative predicted values, measurement-to-delivery intervals, golden standards, and best cutoff values as determined by using receiver operator characteristics curves (ROC curves).

Figure 4E:
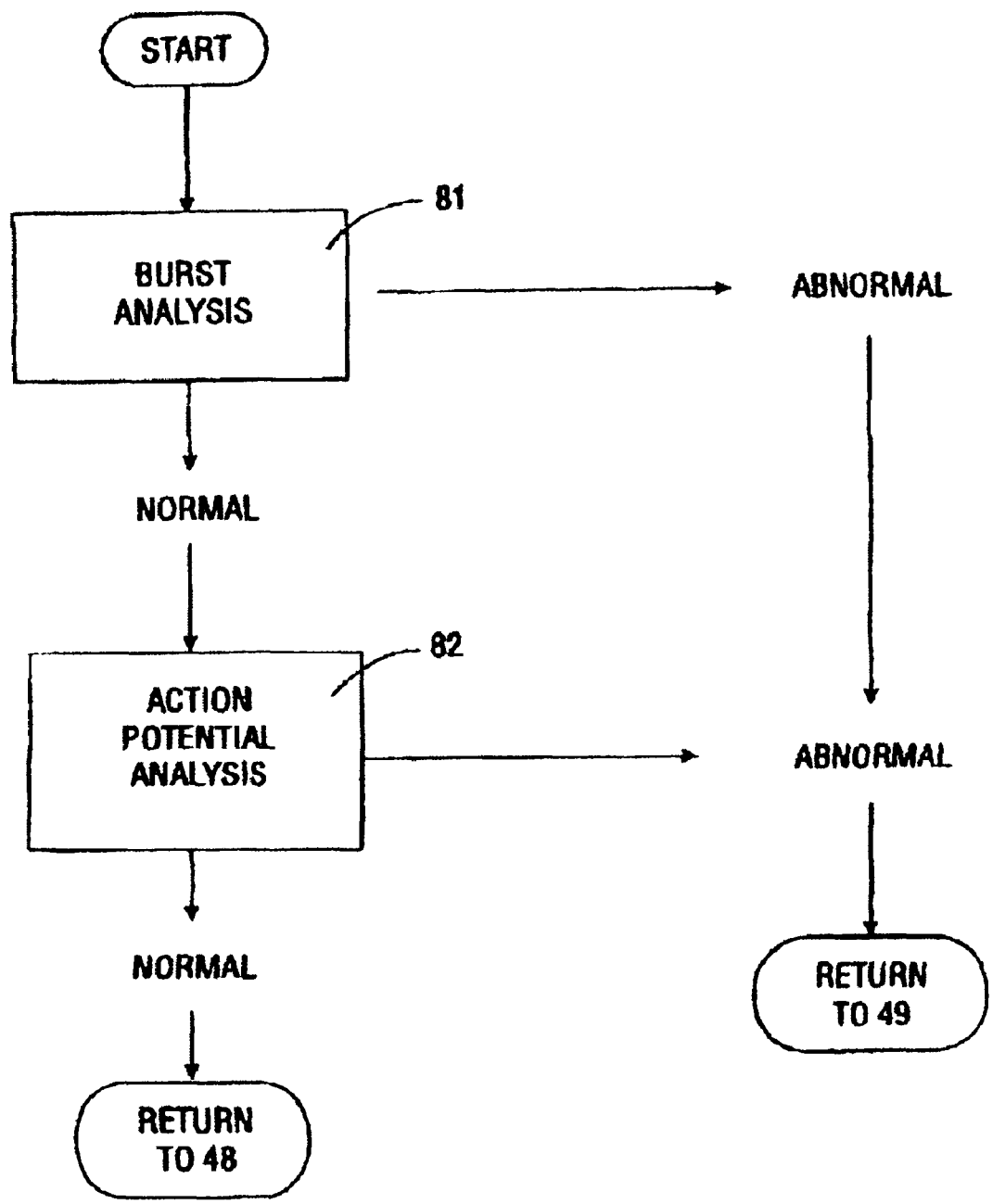

FIG. 4E presents the details of the diagnosis from block 47, shown in FIG. 4A. For purposes of illustration, the below discussion of blocks in FIG. 4E refer to various blocks in FIGS. 4A and 4C. Data from uterine bursts and uterine action potentials probability analysis (block 46) pass to blocks 81 and 82 respectively and recorded burst and action potentials are compared to known normal ranges of values as determined by ROC analysis on previous patient data. Expected values of uterine action potential parameters and uterine burst parameters vary as a function of the classification/clinical data of the patient. When such classification/clinical data are entered into the program, and after the results of uterine signal analysis, using any one or more of the mathematical parameters described in block 65 above, data are compared with normal values. Then an assessment of the normality, abnormality, and predicted time to delivery is made. Control for uterine electrical bursts and individual action potentials information then passes to block 48A if no abnormalities are detected, or to block 49A if any abnormality is detected. A similar procedure for determining normality/abnormality is performed in block 81 for the probability analysis (from block 46) of the maternal and fetal heart rates, QRST complexes, and other cardiac criteria that utilize the bursts (i.e. traces, groups or series of cardiac action potentials) recorded. Likewise normality/abnormality of maternal and fetal cardiac activity is determined in block 82 using probability data (from block 46) of individual cardiac action potentials recorded. Data on the probability analysis of maternal and fetal cardiac electrical "bursts" (i.e. traces, groups or series of cardiac action potentials) and individual cardiac action potentials pass to blocks 81 and 82, respectively, where they are compared to normal values. Once patient classification/clinical data for a patient are entered into the computer, and after the results of cardiac signal analysis, using any one or more of the mathematical parameters described in block 65 above, data are compared with normal values. Then an assessment is made as to the normality/abnormality of the maternal and fetal cardiac activity. Control for maternal and fetal cardiac electrical bursts and individual action potentials information then passes to block 48B if no abnormalities are detected, or to block 49B if any abnormality is detected. Similarly, probability data (from block 46) on fetal brain "bursts" (or traces or groups or collections of action potentials) and individual action potentials pass to blocks 81 and 82, respectively, where they are compared to normal values. Once patient classification/clinical data are entered into the computer, and after the results of fetal brain signal analysis, using any one or more of the mathematical parameters described in block 65 above, data are compared with normal values. Then an assessment is made as to the normality/abnormality of the fetal brain activity. Control for fetal brain electrical bursts and individual action potentials information then passes to block 48C if no abnormalities are detected, or to block 49C if any abnormality is detected.

From the foregoing description, one skilled in the art may easily ascertain the essential characteristics of this invention, and without departing from the spirit and scope thereof, may make various changes and modifications of the invention to adapt it to various usages and conditions.

The present method and apparatus may also be used to measure normal and abnormal function of other smooth muscle tissue, such as that of the bladder and lower gastrointestinal tract. Both organs depend upon smooth muscle contractility to perform their respective functions. Thus, electrical activity of the bladder and bowel may be registered from the abdominal surface during respective urination or defecation, in order to estimate appropriate and abnormal electrical activity of these organs.

The analysis of EMG activity by abdominal surface recording to determine uterine contractility is further discussed in Buhimschi and Garfield, Uterine Contractility as Assessed by Abdominal Surface Recording of EMG Activity, published in AM. J. OB/GYN, 1996; 174:744–53 (February 1996).

Figure 5A:
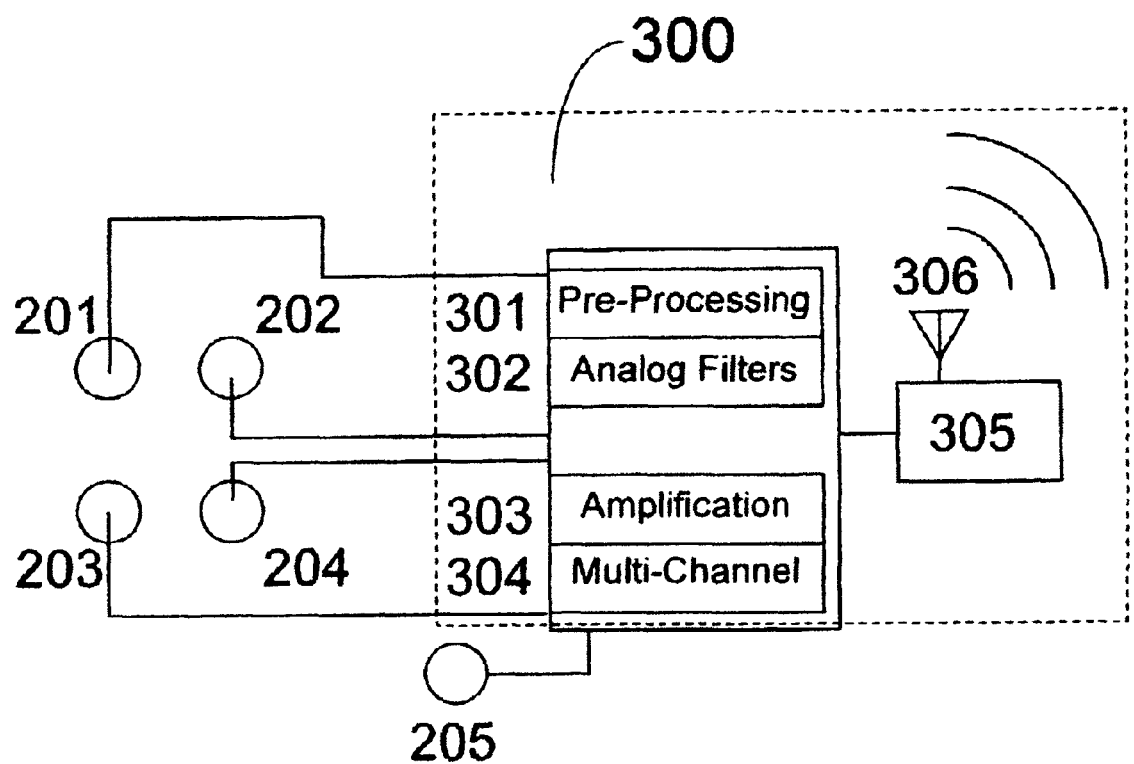
FIG. 5A is a schematic diagram of one embodiment of the present invention as a remote or "home" uterine/cardiac/brain monitoring system.
Figure 5B:
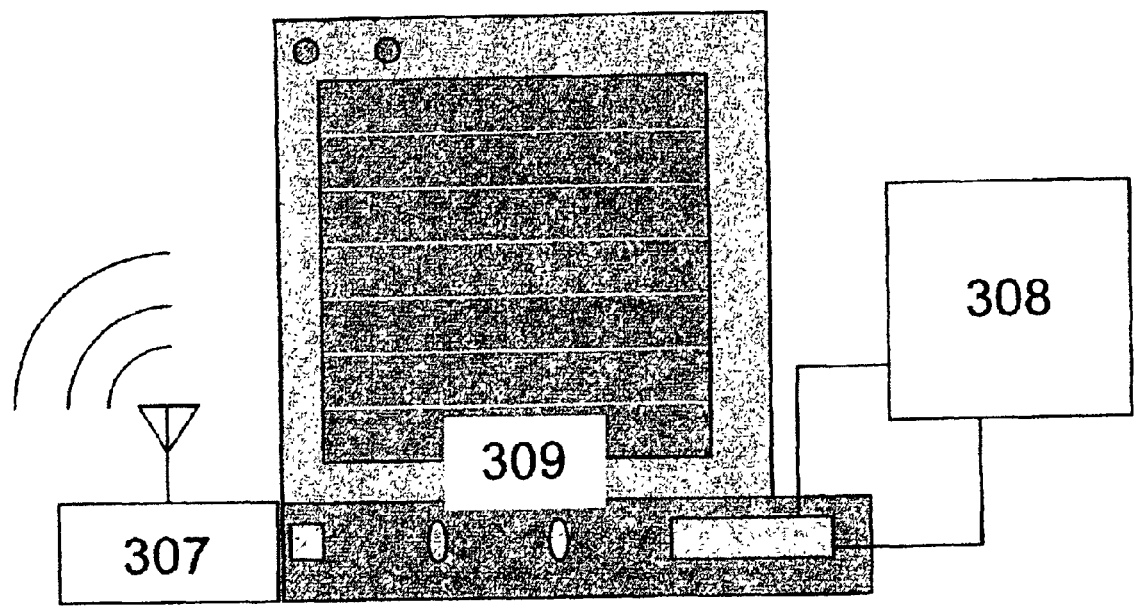
FIG. 5B is a schematic diagram of a central processing unit at a remote location.
Figure 5C:
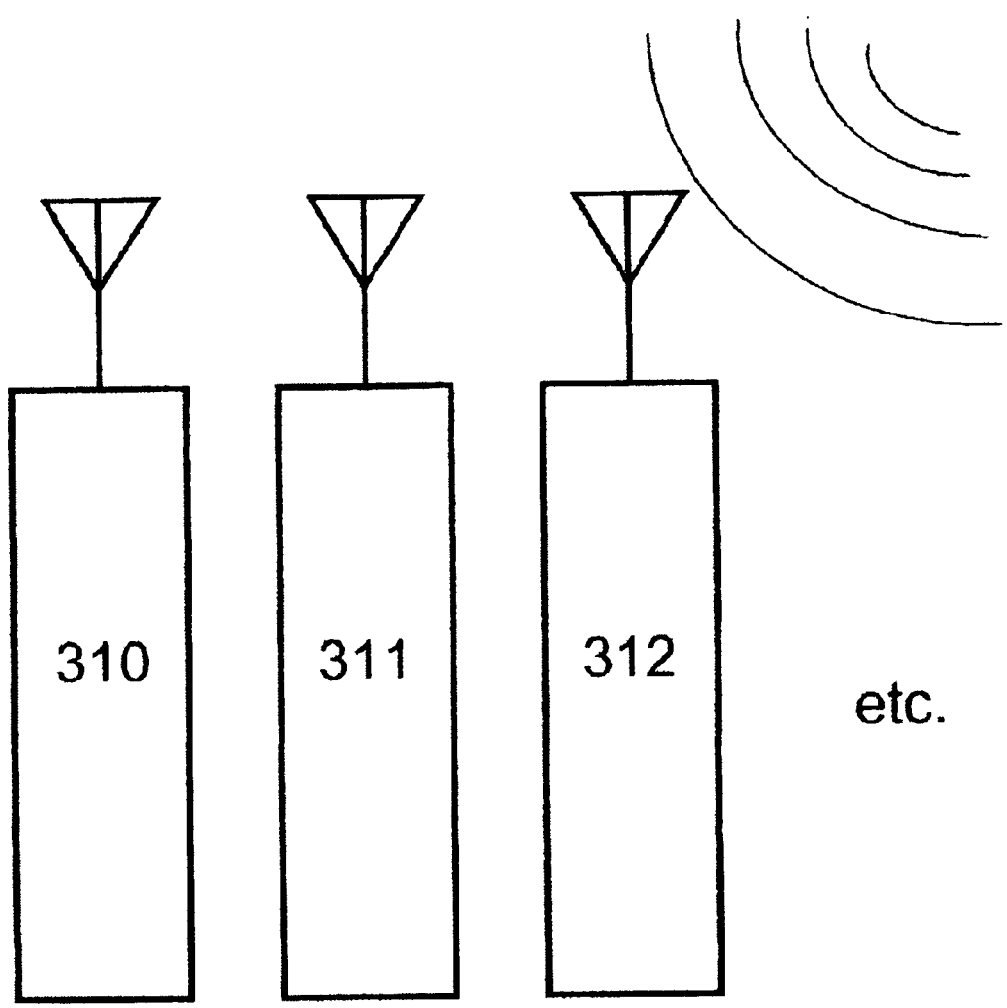
FIG. 5C is a schematic diagram showing cell-phones, pagers, fax machines, and other devices that are communicative to the patient's doctors, family members, friends, and others where information about the patient and fetus, as assessed by the present invention, is sent via wireless or other communication.

FIGS. 5A, 5B, and 5C show an at-home or out-patient monitoring system, which will be realized with the uterine EMG instrument by transmission of uterine EMG and electrical maternal and fetal cardiac and fetal EEG data via landline or transmitter to satellite or other digital or wireless communications systems, and to communications receivers, such as cellular phones, pagers, e-mail boxes, etc. of pertinent personnel, such as doctors, nurses, spouses, family members, and the like. Transmission of this data will also be made to a central processing unit and there it can also be analyzed and/or stored. Such a wireless transmission system could, for example, utilize Blue Tooth technology or other technology to transfer communications. Transmission of patient data is done automatically according to pre-programmed computer instructions of the uterine EMG/EKG/EEG machine or manually by patient or caregiver whenever necessary or desired, and can be done in real-time or with data stored in computer files in the uterine EMG device internal memory. Transmitted data may be either raw data or processed data, as desired, as a signal processing unit with identical capabilities to the machine described in FIG. 1 above and described thereafter will be incorporated into the patient monitoring unit as well as in the central unit, allowing processing/analysis capabilities at the site of the patient and acquisition unit, as well as at a remote "central" location.

FIG. 5A is a schematic diagram of one embodiment of the present invention as a remote or "home" uterine/cardiac/brain monitoring system. In at least one exemplary embodiment, FIG. 5A shows the patient-monitoring unit and depicts a quadra-polar uterine EMG data acquisition system, although other numbers of electrodes can be used. The multi-polar arrangement of surface electrodes 201, 202, 203 and 204 are placed in any configuration desired upon the abdominal, vaginal, or cervical surface of the patient to be monitored. The diagram depicts one possible configuration: the vertical and horizontal electrode spacing could be about 3 cm from electrode center to electrode center, for example, and the array could be located in such a way as to center around the patient's navel. Another example could involve incorporating the acquisition electrodes onto an electrically neutral phallic object, for placing and maintaining electrodes into position along the vaginal wall in any desired configuration. The cervix could also serve as the surface for acquisition. Electrode(s) 205 represents a reference electrode(s), to be placed remotely, or laterally, on the patient, away from the uterus/vagina. Examples of possible electrodes used are: 3-M EKG, Quinton Quik-Prep EKG, or Dantec EEG gold cup electrodes, but these are not the only possible electrodes that could be used. Electrodes could be used in conjunction with electrically conductive epoxy or paste/gels for impedance reduction and conductivity improvement.

The electrical potentials at surface electrodes 201, 202, 203, and 204 are then fed to unit 300, which contains a series of signal pre-processors 301, analog signal filters 302, differential amplifiers 303, and a multi-channel noise reduction unit 304, an expert system 305, and a transceiver 306, in the depicted patient monitoring unit 300. Filters 302 and amplifiers 303 considered collectively function equivalently to filters/amplifiers 20 of FIG. 1. Again in FIG. 5A, the filter bank in analog signal filters 302 is such that any and all potential signals acquired are analog filtered as desired (for example, band-pass filtered from 0.001 Hz. to 3.000 Hz for uterine EMG, or from about 1.0 Hz to 100.0 Hz for EEG analysis, etc.). High and low-pass filter settings can be individually and independently adjusted by computer or manually for each differential signal measured.

The differential amplifier bank 303 is such that the potential difference between any and all pairs of individual electrodes are measured and amplified: (201,202); (201, 203); (201,204); (202,203); (202,204); and (203,204), where (x,y) denotes the potential difference taken across electrodes x and y either measured with respect to the reference electrode(s) 205, or measured directly.

The signal pre-processors 301 will have the capacity of inverting, summing, averaging, applying an absolute value function, or any other mathematical manipulation and combination of the input potentials in such a way as to generate the desired superposition or combination of potentials using any one or more of the input signals as desired, either prior to filtering and/or amplification or after such filtering and/or amplification. The operator, through software and hardware, can optionally control this pre-processing of signals. The summed potential(s), or inverted potential(s), or averaged potential(s) of any two or three electrodes can be measured against the summed potential(s), or inverted potential(s), or averaged potential(s) of any and all other groups of one, two and three electrodes. For example: (201,201+203); (201+203,201+204); (201+202+203,202+204); (202+203+204, 203); etc., where x+y denotes the summed or average potential using x and y. There are other possible electrode-comparison combinations, and any or all are incorporated into the capabilities of this system, when considering the function of unit 300. The above list is meant as an example only and is not representative of the entire range of possible configurations or combinations of electrode potentials. Absolute values or other functions applied to channels may be taken prior to or after summing to enhance the signals relative to background noise when combining channels in this way.

Further occurring in the unit 300, containing filters, amplifiers, and possibly preprocessing is the capacity to optionally apply a secondary noise-reduction scheme in multi-channel noise reduction unit 304. Any one or more of the acquired potential signals will be used to remove unwanted noise components additionally from itself and other signals by applying any one or more of a number of multi-channel noise-elimination methods, including, but not limited to singular value decomposition, cross-correlation, auto-correlation, adaptive filtering, and/or matched filtering. The unit 300 will have the capability of determining and/or modifying or maintaining phase relationships, if necessary, between various channel combinations in order to carry out such noise-reduction utilizing these methods.

All above descriptions of FIG. 5A also apply for the tri-polar configuration, which would simply involve the elimination of one of the electrodes 201, 202, 203, or 204, and elimination of the appropriate number of filters/amplifiers, or for any multi-polar configuration by simply adding or subtracting electrodes or electrode pairs as desired and filters/amplifiers as appropriate. The higher the number of electrodes used in the configuration, the greater the number of possible combinations of channels, or potentials.

After acquiring, optionally pre-conditioning and/or processing, analog filtering, amplifying and, and further reducing noise with a multi-channel filtering method the patient uterine signals, maternal or fetal cardiac, and fetal brain, such as EEG, signals, the data are optionally processed and analyzed at expert system 305, where exists an expert system containing a computer with data analysis programs, storage memory, and optionally a computer display monitor. The processed data, if desired, are fed to the electrical signal detection/analysis subroutine in expert system 305 where uterine contraction events are identified, uterine contraction strength is assessed, fetal cardiac signals are evaluated, fetal EEG is evaluated, and predictions on labor or pre-term labor are calculated. The expert system is able to make predictions about time of delivery and patient and fetus well-being assessments based on these data. The information is then transmitted at transceiver 306 via wireless transmission. Optionally, the unit 300 of FIG. 5A will transmit through transceiver 306 either raw or processed or analyzed data or simply the results of the data processing/analysis or text or audio messages concerning the results of the data or processed/analyzed data. Note that many of the routines delineated in other units of unit 300 could be completed in expert system 305, alternatively.

In a preferred embodiment, signals acquired at the electrodes could be routed through very short leads (less than 12 inches length, for example), could be pre-amplified and then sent to unit 300 by a wireless transmitter instead of by cables or wires. In this case, the acquisition unit consisting of electrodes/short leads/pre-amp/transmitter would be very compact (easily worn on a belt or under the shirt of the patient), and therefore the patient could be mobile and could carry on routine daily activities. This alternative embodiment could also be implemented for in-clinic patients as well as "at-home" or remote outpatients.

In another preferred embodiment, such compact acquisition unit would be waterproof.

In another embodiment, such compact acquisition unit could have one or more of the components 301, 302, 303, and 306 built directly onto or into one or more of the surface electrodes 201, 202, 203, 204, and/or 205 for example, so that no lead wires would be required in the design. Signals partially processed by components 301, 302, and/or 303 could then be transmitted from transceiver 306 to a remote or central unit for further processing.

FIG. 5B is a schematic diagram of a central processing unit at a remote location. Data transmitted from transceiver 306 will be optionally received at a central station, or unit as seen in FIG. 5B, controlled by the main expert system 309, where the signal is received at a transceiver 307 and, if desired, sent to an optional digital signal conditioning unit 308, which applies cross-correlation, adaptive, auto-correlation, matched, or singular value decomposition and any other desired digital signal processing to the data. In alternative embodiments, these conditioning of signals and/or noise-reduction techniques could occur either prior to or after amplification of signals. The processed data, if desired, are fed to uterine burst detection/analysis and maternal and fetal cardiac and fetal brain electrical activity analysis subroutines in the main expert system 309 where uterine contraction events are identified, uterine contraction strength is assessed, fetal cardiac signals are evaluated, fetal EEG is evaluated, and predictions on labor or pre-term labor are calculated. The main expert system 309 is able to make predictions about time of delivery and patient and fetus well-being assessments based on these data. The main expert system 309 can display all information and then, if desired, transmit the raw data or processed/analyzed data or simply the results of the data or text or audio messages concerning the results of the data or processed/analyzed data, from transceiver 307. Note that many of the routines delineated could be completed in the main expert system 309, alternatively.

In another preferred embodiment, unit 300 shown in FIG. 5A would carry out a limited number of the tasks previously described for unit 300, and with the remaining tasks completed at a remote location or central station using the main expert system 309, for example, upon receipt of the partially-processed data from unit 300 through wireless (or other) communication received by transceiver 307 from transceiver 306.

FIG. 5C is a schematic diagram showing cell-phones, pagers, fax machines, and other devices that are communicative to the patient's doctors, family members, friends, and others where information about the patient and fetus, as assessed by the present invention, is sent via wireless or other communication. Data transmitted from either transceiver 306 or alternatively transceiver 307 will be optionally or additionally received at any receiving devices shown in FIG. 5C, including cell phone 310, pager 311, e-mail 312, and other communicative devices and methods, including communications to computer systems for further notification or processing.

Figure 6:
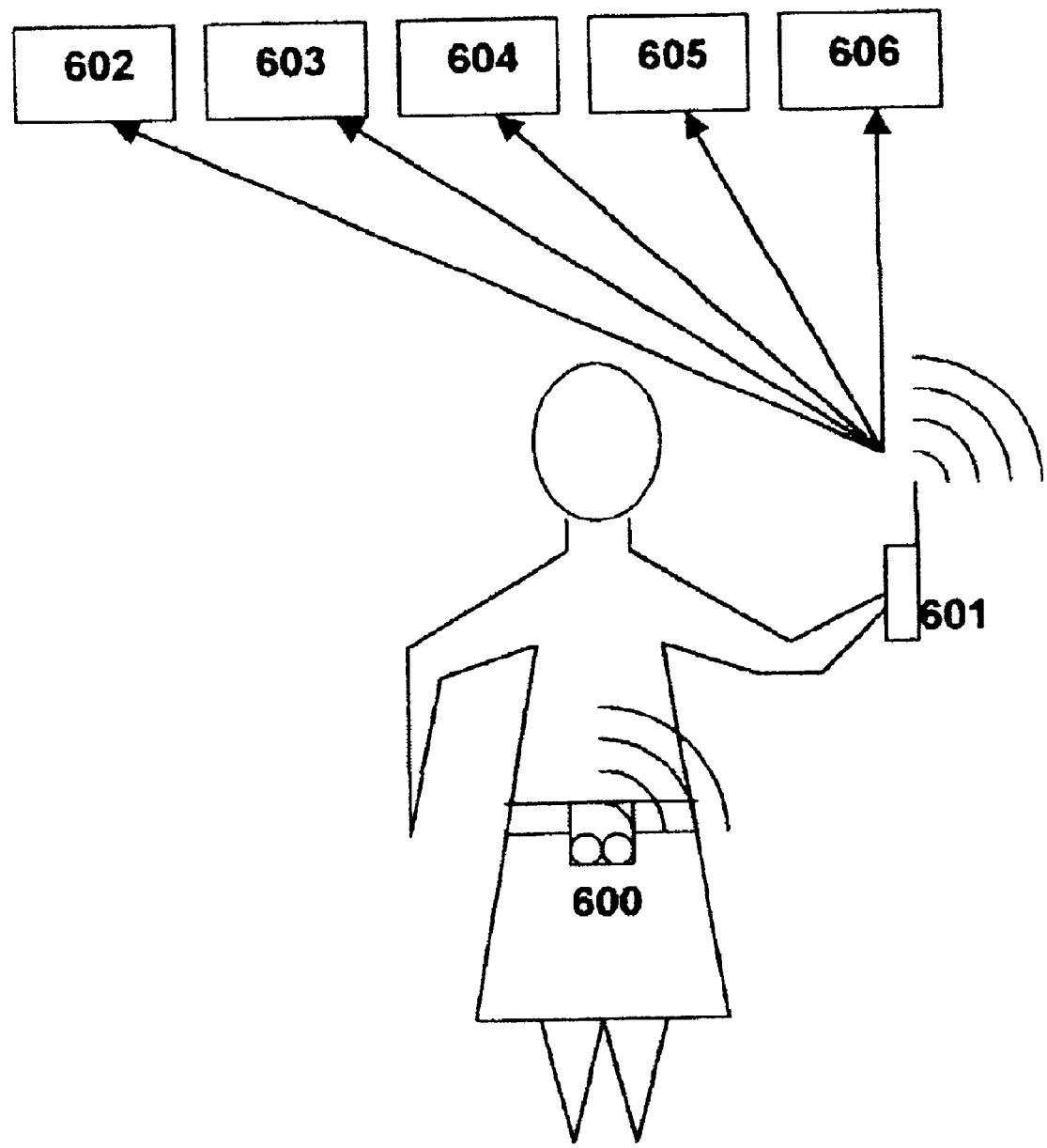
FIG. 6 is a schematic diagram of a representative pregnant patient utilizing an at-home or outpatient version of the present invention.

FIG. 6 is a schematic diagram of a representative pregnant patient utilizing an at-home or outpatient version of the present invention. A representative pregnant patient can wear one possible configuration of the system 600 described herein. The system 600 can transmitting patient information, including the diagnosis of true labor to a handheld cellular phone 601, or other wireless transceiver or other communication means to several destinations, such as child care personnel 602, physicians 603, spouse 604, a base or central processing/monitoring station 605, to the hospital 606, or other devices, locations, personnel, or systems.

Figure 7:
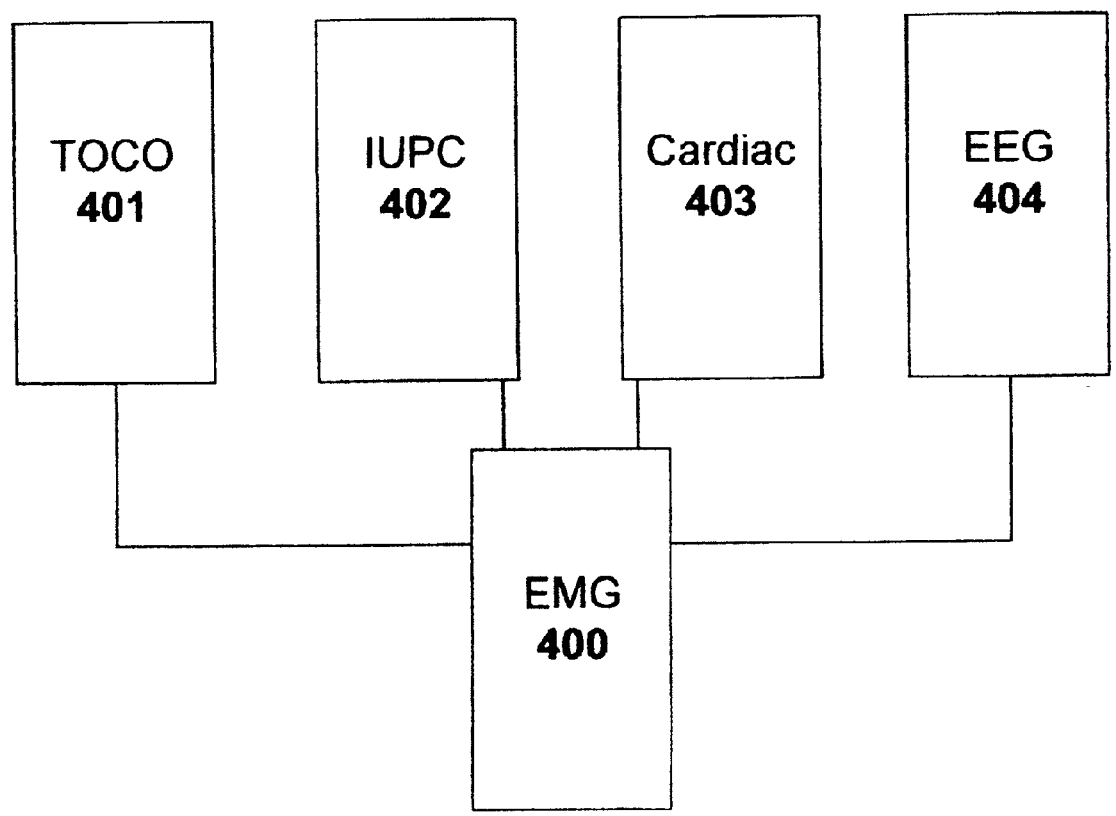
FIG. 7 is a schematic diagram depicting various standard clinical devices that could be used in conjunction with the present invention.

FIG. 7 is a schematic diagram depicting various standard clinical devices that could be used in conjunction with the present invention. FIG. 7 represents some of the possible patient/fetus monitoring components that could be incorporated into the present invention, or could be used in conjunction with the present invention as a separate unit: electromyography unit 400, tocodynamometer unit 401, intrauterine-pressure catheter unit 402, maternal/fetal cardiac unit 403, and fetal brain unit 404. This list does not exclude the possibility of including other devices that could operate in conjunction with, or be incorporated into the design and/or operation of the present invention. In a preferred embodiment, units 401, 402, 403, 404 optionally communicate with unit 400, but are not necessarily required to communicate with each other. Some of the components may already be considered standard equipment used presently in the clinic. Further description of these optional units is given below:

Electromyography Unit (400): measures uterine electrical activity, and converts the uterine electrical data to forms representing contractions, intensity of contractions, contraction duration and time, fetal heart rate, fetal EEG, and/or intrauterine pressure, via abdominal surface, vaginal, or cervical electrodes, using any one or more of the following analytical methods, processes, or parameters: frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis. The electromyography unit 401 encompasses, in a quadra-polar arrangement of electrodes, for example, surface electrodes 201, 202, 203, and 204, reference electrode(s) 205, signal pre-processors 301, analog signal filters 302, amplifiers 303, and multi-channel filters 304 of FIG. 5A, combined, as well as computer, data storage and all processing/analysis/prediction capabilities. The unit 400 may be of the in-clinic or at-home variety of the present invention described elsewhere above.

Tocodynamometer (TOCO) Unit (401): measures contractions events by mechanical pressure transducer or other method, including duration and time and relative to intensity. This unit could be Hewlett-Packard or other brand.

Intrauterine Pressure Catheter (IUPC) Unit (402): measures intrauterine pressure by means of a fluid-filled catheter and relates this to intensity of contractions. This device could be Hewlett-Packard or other brand.

Maternal/Fetal Cardiac Unit (403): measures heart rate and cardiac QRST tracings and other cardiac parameters of the mother and/or fetus via Doppler ultrasound, pulse oximetry and/or or other methods. This unit could be Hewlett-Packard or other brand.

Fetal Brain Unit (404): measures fetal EEG or ECOG or other fetal brain electrical activity, utilizing scalp electrodes or other methods to acquire brain electrical signals from the fetus. This unit could be Hewlett-Packard or other brand.

The present invention may also be used to predict treatment for a pregnant woman. The data signals collected can be analyzed by the present system and compared to existing norms to indicate the appropriate pharmacological treatment depending upon the uterine activity. For example, when uterine signal levels are low and indicative of non-labor, a term patient can be treated in such a fashion pharmacologically to induce labor (i.e., oxytocin, prostaglandins, etc.). When uterine signal levels are high in a patient prior to term (i.e., pre-term labor) treatment can consist of use of uterine inhibitors to suppress labor (e.g., tocolytic agents, β-agonists, calcium channel blockers, etc.). As one of skill would understand, other obstetric diagnosis treatments could be predicted using the present invention. Similar pharmacological treatments for maternal and fetal cardiac or fetal brain abnormalities can be rendered for high or low maternal and fetal cardiac activity or high or low fetal brain activity based upon the appropriately acquired and processed maternal and fetal cardiac and fetal brain signals.

From the techniques described above, digital analysis techniques have now been developed and further improved to analyze further the surface electrical activity, or EMG, for obstetrical diagnosis and characterization of uterine, maternal and fetal cardiac and fetal brain activity (The fetal brain signal is not technically EMG in nature, but will be considered present in the EMG signals acquired trans-abdominally or otherwise, and will be included and considered as effectively equivalent to EMG signals for all EMG signal acquisition, analysis, and processing descriptions and figures which apply to the present invention).

Figure 8:
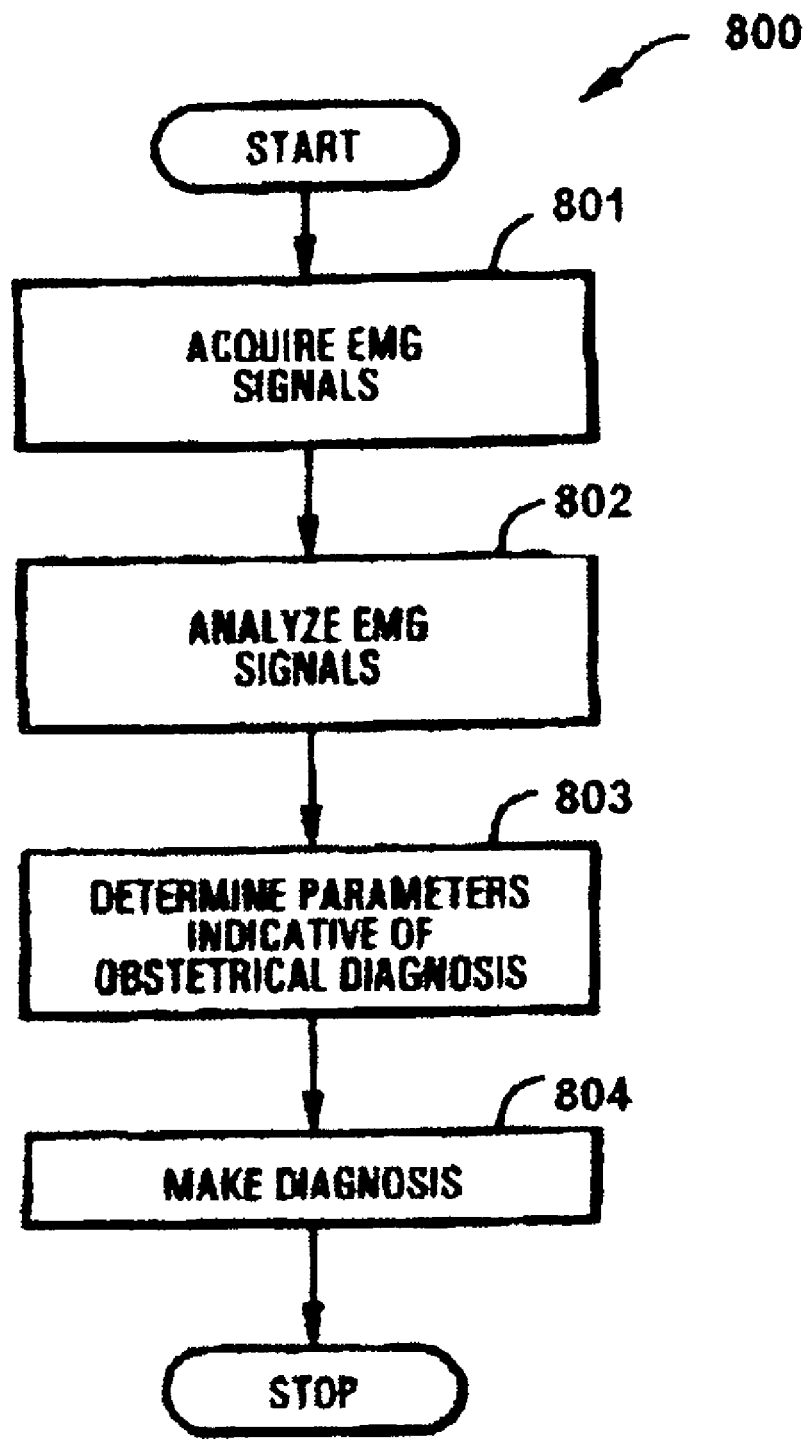
FIG. 8 is a schematic flow chart of a further embodiment of a data processing technique according to the present invention.

FIG. 8 is a schematic flow chart of a further embodiment of a data processing technique according to the present invention. Method 800 for analyzing surface electrical data to characterize maternal uterine, maternal and fetal cardiac and fetal brain activity includes process blocks 801, 802, 803 and 804. In block 801, electrical signals are first acquired, preprocessed and filtered/amplified, etc. After this data is obtained, the signals are analyzed in block 802. Once processed and analyzed, parameters are determined from the signals that are indicative of an obstetrical diagnosis in block 803. Finally, a diagnosis is made or predicted in block 804. Within this general framework, a wide variety of data analysis techniques may be employed to analyze electrical signals for obstetrical diagnosis.

These analysis techniques or methods, as applied to the acquired uterine, maternal and fetal cardiac, and fetal brain electrical signals, may include utilizing or evaluating the following parameters, methods or techniques, or evaluating or interpreting changes in these: frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, and/or other joint time-frequency analysis.

These analytical systems provide important information on uterine activity, maternal and fetal cardiac activity, and fetal brain activity that can be used for diagnosis. These systems are based upon the recording of electrical activity from the abdominal surface, for example, as described above. The abdominal electromyogram (EMG), or electrohysterogram (EHG), the maternal and fetal ECG, or EKG, and the fetal EEG or ECOG, may be analyzed and the resulting analysis used to facilitate the clinical evaluation of uterine activity and maternal and fetal well-being during pregnancy. The present invention may also be utilized for the early diagnosis of abnormal uterine contractility, abnormal maternal and fetal cardiac activity, and abnormal fetal brain activity by analyzing the electrical signals. For uterine activity, such diagnoses take advantage of the characteristic that uterine electrical activity gradually changes during the last month of pregnancy until parturition. Weak and localized at the beginning of labor, this electrical activity becomes stronger, rhythmical and well propagated during labor. EMG, therefore, offers much information about both excitation and propagation of uterine activity.

In a preferred embodiment, the maternal uterine, maternal and fetal cardiac, and fetal brain activity may be analyzed by determining (a) the mean frequency of a plurality of action potentials in at least one measured burst, (b) the starting frequency of action potentials in at least one measured burst, and (c) the ending frequency of action potentials in at least measured burst. In another preferred embodiment, the maternal uterine, maternal and fetal cardiac, and fetal brain activity may be analyzed by determining the rate of rise of amplitude in at least one action potential, and the rate of fall of amplitude in at least one action potential.

The following data analysis techniques are based upon analyses of electrical uterine, maternal and fetal cardiac, and fetal brain signals using various approaches, and represent different definitions and calculations of these parameters:

A. Fourier Analysis

Any method of electrical burst or signal detection or comparison which relies upon Fourier parameters including, but not limited to Fourier Transform, Fast Fourier Transform, Amplitude Adjusted Fourier Transform, Iterated Amplitude Adjusted Fourier Transform (with either power spectrum or amplitude discrepancy), Power Density Spectrum, or parts thereof, and spectral-temporal mapping (STM), etc., or parts thereof, for the purpose of discerning uterine EMG, fetal cardiac, and fetal EEG signal properties, or differences therein relative to other signals or portions thereof, or relative to the background (non-uterine, fetal cardiac or fetal EEG signals) which may be recorded and are generally considered as noise. Further details for those skilled in the art may be found in the following reference: *Introduction to Fourier Analysis. Morrison N.*, 1994, John Wiley and Sons.

B. Wavelet Analysis

Any method of electrical burst or signal detection or comparison which relies upon wavelet parameters including, but not limited to wavelet coefficients, spline functions, scales, or percent-energy distribution of signals through wavelet sub-bands, or scales, etc., or parts thereof, for the purpose of discerning uterine EMG, fetal cardiac, and fetal EEG signal properties, or differences therein relative to other signals or portions thereof, or relative to the background (non-uterine, fetal cardiac or fetal EEG signals) which may be recorded and are generally considered as noise. Further details for those skilled in the art may be found in the following reference: *Wavelets and Filter Banks. Strang G.*, 1996, Wellesy-Cambridge Press.

C. Complexity or Randomness

Any method of electrical burst or signal detection or comparison which relies upon complexity or randomness parameters including, but not limited to eigenvalues, eigenfunctions, primitive and exhaustive histories, or Limpel-Ziv (LZ) complexity measure, etc., for the purpose of discerning uterine EMG, fetal cardiac, and fetal EEG signal properties, or differences therein relative to other signals or portions thereof, or relative to the background (non-uterine, fetal cardiac, or fetal EEG) signals which may be recorded and are generally considered as noise. Further details for those skilled in the art may be found in the following reference: *On the Complexity of Finite Sequences. Lempel A, IEEE Trans Informn. Theory*, 1976:22; 75–88.

D. Zero-Crossings

Any method of electrical burst or signal detection or comparison which relies upon zero-crossing parameters including, but not limited to zeroth-order, first-order, and higher-order crossing counts, etc., for the purpose of discerning uterine EMG, fetal cardiac, and fetal EEG signal properties or differences therein relative to other signals or portions thereof, or relative to the background (non-uterine, fetal cardiac, or fetal EEG) signals which may be recorded and are generally considered as noise. Further details for those skilled in the art may be found in the following reference: *Spectral Analysis and Discrimination by Zero-Crossings. Kedem B, Proceedings of the IEEE*, 74:11; 1477–93.

E. Fractals or Multifractals

Any method of electrical burst or signal detection or comparison which relies upon fractal parameters including but not limited to, Hurst Exponent, Fractal Dimension, or Beta values in analytic methods, including, but not limited to R/S (range/standard deviation), Power Spectrum, Roughness-Lengths, Variograms, and Wavelet analyses, etc., for the purpose of discerning uterine EMG, fetal cardiac, and fetal EEG signal properties, or differences therein relative to other signals or portions thereof, or relative to the background (non-uterine, fetal cardiac or fetal EEG signals) which may be recorded and are generally considered as noise. Further details for those skilled in the art may be found in the following reference: *Multifractals: Theory and Application. Harte D*, 2001, CRC Press.

F. Nonlinearity and Chaos

Any method of electrical burst detection or comparison which relies upon Non-Linearity or Chaos parameters including, but not limited to entropy, approximate entropy, Kolmogorov-Smirnov statistics, or Chaoticity, etc., for the purpose of discerning uterine EMG signal properties, or differences therein relative to other signals or portions thereof, or relative to the background (non-uterine, fetal cardiac or fetal EEG) signals which may be recorded and are generally considered as noise. Further details for those skilled in the art may be found in the following reference: *The Nonlinear Workbook: Chaos, Fractals, Cellular Automata. Neural Networks, Genetic Algorithms, Fuzzy Logic with C++ and Reduce Programs.* Willi-Hans Hans Steeb, 2000, World Scientific Press.

G. Likelihood Ratios

Any method for electrical burst detection or comparison which relies upon parameters of likelihood ratios, or local generalized likelihood ratios including, but not limited to adaptive cumulative sums, and dynamic cumulative sums, etc., for the purpose of discerning uterine EMG signal properties, or differences therein relative to other signals or portions thereof, or relative to the background (non-uterine, fetal cardiac or fetal EEG) signals which may be recorded and are generally considered as noise. Further details for those skilled in the art may be found in the following reference: *Likelihood Methods in Statistics.* Severini T, 2001, Oxford University Press, Incorporated.

H. Statistical Methods

Any method for electrical burst detection or comparison which relies upon parameters of statistical methods, including, but not limited to means, standard deviations, variances, expected values, discreet or continuous random variables, Decision Statistics, Inter-rater statistics, or ratios or functions of one or more of these statistical parameters, etc., for the purpose of discerning uterine EMG signal properties, or differences therein relative to other signals or portions thereof, or relative to the background (non-uterine, fetal cardiac or fetal EEG) signals which may be recorded and are generally considered as noise. Further details for those skilled in the art may be found in the following reference: *Statistical Signal Processing, Louis L. Scharf*, 1991, Addison Wesley Longman, Incorporated.

I. Wigner-Ville or Heisenberg-Gabor Analysis

Any method for electrical burst detection or comparison which relies upon parameters of Wigner-Ville or Heisenberg-Gabor Analysis, including, but not limited to Guassian, Fourier, or Dirac distributions, expectation values, duration-bandwidth products, adaptive and evolutionary and moving and joint methods, and spectrogram and discretization methods, and atomic decomposition and s-Wigner distributions, for the purpose of discerning uterine EMG signal properties, or differences therein relative to other signals or portions thereof, or relative to the background (non-uterine, fetal cardiac or fetal EEG) signals which may be recorded and are generally considered as noise. Further details for those skilled in the art may be found in the following reference: *Time-Frequency/Time-Scale Analysis.* Patrick Flandrin, 1999, Academic Press.

Uterine electrical data for many patients, processed and analyzed using any one or more of the above described mathematical techniques or parameters, may be collected to provide a knowledge base from which to predict future uterine activity based upon one or more identified trends in a patient's examined uterine activity indicating parameters. In performing a predictive analysis an identified trend in the patient's examined uterine activity indicating parameters is compared to other trends in the knowledge base of an expert system. When matching trends are found between the patient's trends and trends in the expert system for an identified time period, a prediction is made regarding future uterine activity based upon how the matching trends in the knowledge base have behaved beyond the time period. Similar comparisons of maternal and fetal cardiac signals and fetal brain signals to known normal values will help to determine maternal and fetal well-being.

Figure 9:
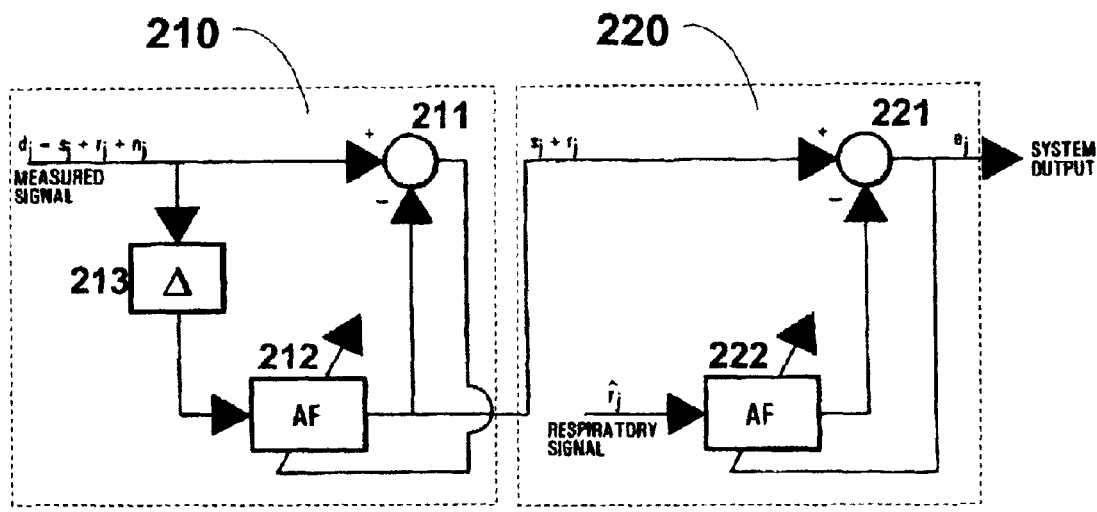
FIG. 9 is a schematic diagram of a portion of the invention for reducing noise in electrical activity signals.

FIG. 9 is a schematic diagram of a portion of the invention for reducing noise in electrical activity signals. An adaptive filter system is shown, which consists of the Adaptive Line Enhancer (ALE), 210, and the Adaptive Noise Canceller (ANC) 220. The components for these systems are available from Newark Electronics, Chicago, Ill. Both filters could use a LMS (least mean square) algorithm, for example.

In operation, the main signal $d_j$, which includes the EMG signal or primary signal ($s_j$), is band-pass filtered with bandwidth 0.001–3.0 Hz, for example, before adaptive filtering. An adaptive line enhancer (ALE) 210, consisting primarily of a summer 211, an adaptive filter 212, and a delay 213, is used to eliminate the background noise $n_j$ from the primary signal $s_j$. The delay 213 is chosen as one constant according to practical experiments to de-correlate the periodic and correlated signals $s_j$ and $r_j$ from $n_j$. The adaptive noise canceller (ANC) 220, consisting primarily of a summer 221 and an adaptive filter 222, is used to filter out respiratory noise ($r_j$), for instance. Here, a respiratory signal is also a reference signal ($r_j$) of the ANC. A respiratory reference signal could be recorded by positioning a pressure transducer on the chest above the diaphragm, for example.

Thus, the Adaptive Line Enhancer (ALE) 210, portion of the adaptive system functions as a preprocessing unit to eliminate the background noise $n_j$. The Adaptive Noise Canceller (ANC) 220 can be used to eliminate respiratory artifacts ($r_j$), for example. After the processing, an enhanced main EMG signal ($s_j$) is acquired and may be analyzed. Other sources of noise, particularly of a biological nature, may similarly be removed with this technique.

1. Potential Vector Analysis Using Vectorhysterograms

A vector analysis of action potentials may also be used to determine useful parameters for obstetrical diagnosis. The uterine electromyogram is the result of electrical activity generated at the cellular level. The potential at any arbitrary point on the abdominal surface, back and sides from a pregnant woman may be measured and recorded, and the whole uterus can be modeled as a dipole vector. If the vector represents the spread of uterine myometrium excitation, the orthogonal component of the vector can be recorded. The orthogonal vector component $P_x(t)$, $P_y(t)$ and $P_z(t)$ of the vector P and its direction can be determined and analyzed.

A. General Principles

Body surface potential vector analysis is based on Frank's torso experiment model and research results. In the 1950's, Frank shaped a plaster cast of a subject's body, waterproofed it and filled it with saltwater. He then placed a dipole source composed of two electrodes on a rod within the torso model. From measurements in such experiments, Frank found that the geometrical transfer coefficients that relate the dipole source to each point of the body surface potential $V_n$ (t). Thus for a set of k body surface potentials, there is a set of k equations that can be expressed in matrix from:

$$V=T*P.$$

Here, $V=\{v_1, \ldots, V_K\}^T$; $T=\{T_1, T_2, T_3\}$; $T_1=\{t_{11}, \ldots, t_{1K}\}^T$; $T2=\{t_{21}, \ldots, t_{2K}\}^T$; $T_3=\{t_{31}, \ldots, t_{3K}\}^T$; $P=\{P_x, P_y, P_z\}$. V is a K*1 vector. T is a K*3 transfer coefficient matrix. P is the 3*1 time-varying dipole source vector.

Figure 12A:
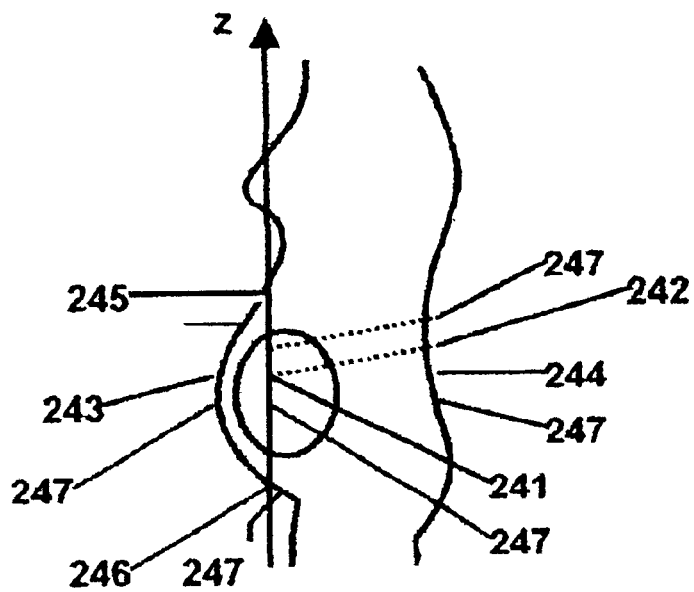
FIG. 12A is a schematic side view of a patient showing the placement of electrodes used for vector potential analysis.
Figure 12C:
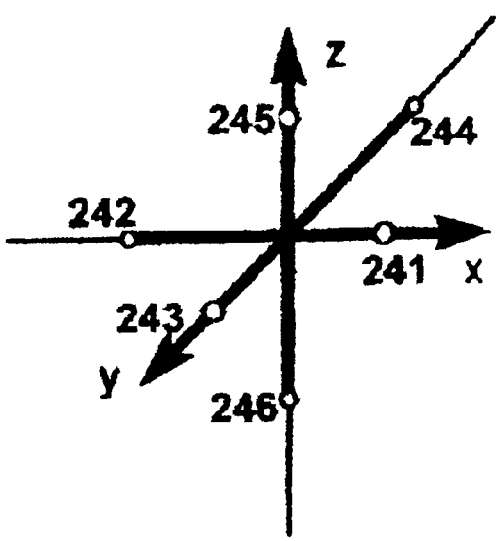
FIG. 12C is a schematic graphic representation of the spatial relationship of the electrodes shown in FIGS. 12A–12B.
Figure 12B:
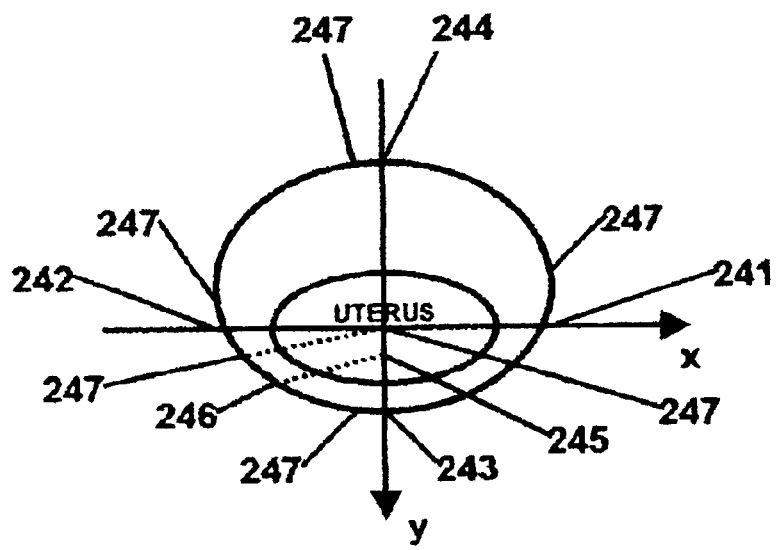
FIG. 12B is a schematic top view of the patient shown in FIG. 12A.

Based upon this dipole analysis, and making the dipole source a uterus of a pregnant women, the potential at any point and at the same time can be measured to obtain the orthogonal vector component of the action potentials on an XYZ axis. An example of the placement of electrodes on a patient, and a 3-dimensional position of electrodes located on an XYZ axis is shown in FIGS. 12A, 12B, and 12C below.

When acquiring the six-point potential at any time, the vector component on X, Y axis at this time is also obtained. It is noted that the direction is that the vector points toward the electrode with higher potential. For example, if $P_x>0$, then the direction is in X positive direction.

During early phases of pregnancy, contractions in the uterus are thought to be driven by pacemakers located randomly in the uterus, so that potentials propagate multi-directionally. Later, as labor approaches, some studies suggest that the potentials become more unidirectional. Knowing whether this transition has occurred in a patient could improve our ability to predict when delivery will occur.

B. EMG Signal Recording and Noise Canceling.

Figure 10:
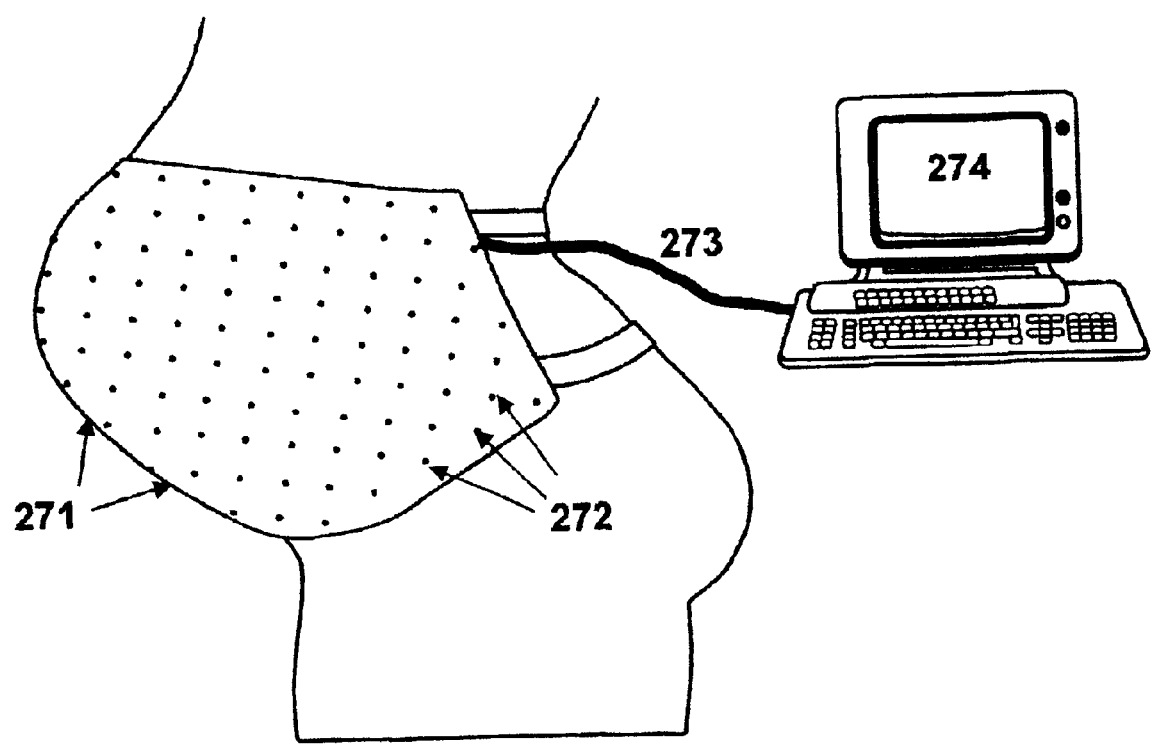
FIG. 10 is a schematic side view of a patient wearing an abdominal belt embedded with a multi-electrode array for determination of uterine potential vectors in two or three dimensions.

FIG. 10 is a schematic side view of a patient wearing an abdominal belt 271 embedded with a multi-electrode array for determination of uterine potential vectors in two or three dimensions. As one non-limiting example, tri-polar groups of Ag/AgCl Beckman electrodes 272, may be used for recording. One or more of the electrodes 272 can be a ground electrode(s). Other arrangements of electrodes may be used, such as quadra-polar, etc. They may be arranged on the abdominal surface, sides and back of a patient. It is also possible to use a fewer or a greater number of electrodes, as shown in FIG. 10. However, for the present invention, at least three are suggested for use. An abdominal sheath is embedded with an array of electrodes from which EMG signals are collected for further processing. Signals are sent through a cable 273 to an expert system 274 capable of performing signal pre-conditioning, filtering, and/or analysis of uterine, maternal and fetal cardiac, and/or fetal brain electrical signals. In other embodiments the coverage of the sheath may be less than or greater than shown here, so that sheath may reach around the back of the patient and higher or lower on the pelvis and torso, and the number of electrodes may be greater than or less than illustrated here and the electrodes may be selectable. An arrangement of ECG-measuring electrodes may also be included for purposes of adaptive noise reduction.

At each point the system records the EMG signals corresponding to uterine contractions, maternal and fetal cardiac activity, and fetal brain activity. A digital signal processing system is used to acquire the EMG signals at each point. The EMG signal at each point will likely be contaminated by noises. The Adaptive Noise Canceller (ANC) and Adaptive Line Enhancer (ANE), or any other filtering techniques may be used to cut off the noises, as discussed previously.

C. Analysis

Six channel EMG signal segments are selected to correspond to the mechanical contact segments of the uterus. Data is then saved into one data file. The data file is then analyzed.

Figure 11:
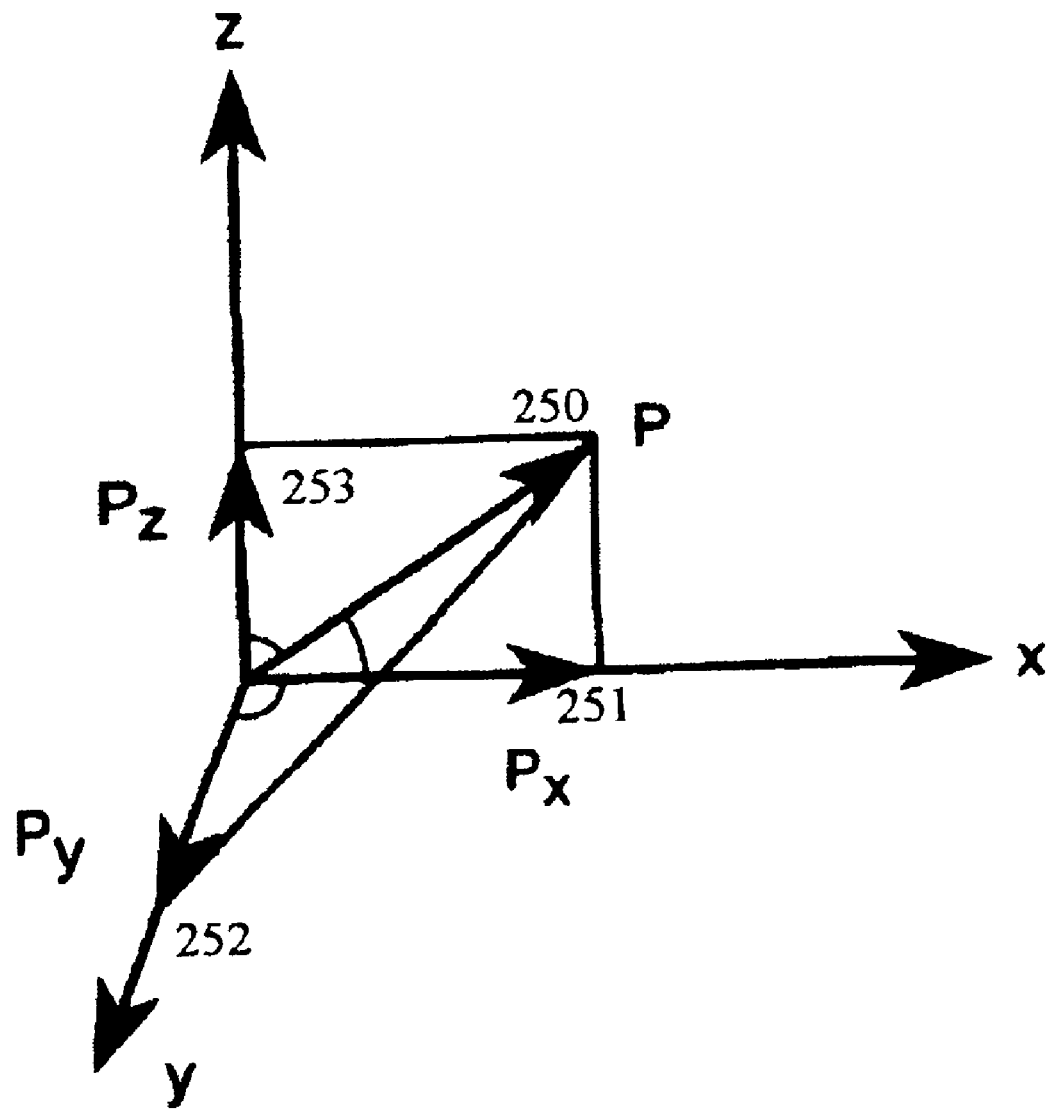
FIG. 11 is a schematic diagram of an electrical potential vector.

FIG. 11 is a schematic diagram of an electrical potential vector P(t) 250. At each sample time, the system can calculate the direction vector $\{P_x, P_y, P_z\}$ of uterine potential vector P(t) 250. $P_x$ 251 is the angle of vector P(t) 250 with X-axis in 3-dimension. $P_y$ 252 is the angle of vector P(t) 250 with Y-axis in 3-dimension. $P_z$ 253 is the angle of vector P(t) 250 with Z-axis in 3-dimension. In order to analyze the data, the orthogonal vector components $P_x$ 251, $P_y$ 252 and $P_z$ 253 are acquired. According to the orthogonal vector component direction, the tracing of uterine potential vector P(t) 250 can be divided into 8 areas in a 3-dimension space. The rules are as follows:

| $P_x$ (t) | $P_y$ (t) | $P_x$ (t) | Area No. |
|---|---|---|---|
| + | + | + | 1 |
| − | + | + | 2 |
| − | − | + | 3 |
| + | − | + | 4 |
| + | + | − | 5 |
| − | + | − | 6 |
| − | − | − | 7 |
| + | − | − | 8 |

The present system may display the vector P(t) 250 tracing in 3-dimension on a computer screen. The user can select the demonstration speed that controls the tracing on screen. When the lower speed is selected, the details of the tracing changes at each sample time can be easily observed.

The system supports another method to assist the user to analyze the changes in progression of P(t) 250 at each sample time. At each sample time $t_i$, the system will determine which area vector $P(t_1)$ should be in according to the rules of area division. The system will draw out the change in progression in order of P(t) 250 as follows:

Time: $t_0$  $t_0 + \Delta t$
  $t_0 + 2\Delta t$
   $t_0 + 3\Delta t$ . . .
Order:
  1 to   3 to   5 to   6 to . . .
Angle:
  {12, 24, 53} to
    {23, 54, 12} to
      {3, 23, 15} to
        {13, 34, 60}
          to . . .

The results can be displayed on-screen or may be printed on a printer. Using this method the vector of activity can be defined, and the origin and spread of activity may also be defined. Further, pacemaker regions and direction of propagation of uterine electrical activity may be identified. These parameters may then be used to characterize women as labor or non-labor, may assist with predicting necessary treatments of pregnant women, or facilitate making other obstetrical diagnoses. In the present invention, a similar treatment also using vector analysis can be performed to monitor and/or characterize the maternal and fetal cardiac electrical activity as well as fetal brain activity.

2. Other Data Analysis Techniques

As would be obvious to one of skill in the art, other analytical techniques may be utilized to analyze the uterine electrical activity data described above.

Acquiring potentials from the surface of a patient using multiple electrodes 241–246 as shown in FIGS. 12A–12C, a field of vectors representing electrical activity at various points on the uterine surface can be constructed. A number of ground electrodes, 247, commensurate with the number of acquisition electrodes used, will be placed on the surface of the patient as indicated.

FIG. 12A is a schematic side view of a patient showing the placement of electrodes used for vector potential analysis. FIG. 12B is a schematic top view of the patient shown in FIG. 12A. FIG. 12C is a schematic graphic representation of the spatial relationship of the electrodes shown in FIGS. 12A–12B. The figures will be described in conjunction with each other. Possible locations for ground electrodes, 247, are also displayed in FIG. 12A and FIG. 12B. The field information obtained can be used to characterize the behavior of the electrical activity locally by mapping the vector at each point onto an ovoid surface. The vectors can be analyzed according to the discussion above regarding FIG. 11, for example. The appearance of the map may be useful in staging labor or pre-labor and in identifying conduction anomalies. In addition to providing information about overall conduction, this data will also evaluate the homogeneity of the electrical behavior at a number of locations on the surface of the uterus. These data can help to localize excitation spots and dead zones. In one embodiment, one of more electrodes 241–247 can be affixed to a belt that is worn by the patient, as shown in FIG. 10.

One alternative technique is to integrate the energy measured for a burst of action potentials. Using this technique, the electrical signals in a burst of action potentials recorded from the uterus are first squared, then summed and the total area under the curve is then integrated. This analysis gives a rough estimate of the energy within a burst of action potentials. It does not, however, account for the length or time component of the data measured. Thus, this analysis could be extended by further dividing the approximate total energy for the burst of action potentials by the total time of the burst to determine the integrated function/time value or energy per unit time for the burst.

Another alternative technique for analysis of uterine activity is to determine burst energy by taking a power spectrum of a uterine burst electrical signal, and then summing the power components in the uterine frequency range, from 0.34 Hz. to 1.0 Hz, for example, (in order to only consider uterine components, rather than respiratory or movement artifact components, which sometimes interfere with the uterine signal at less than 0.34 Hz). Then the sum of the power components for the uterine signal can be multiplied by the time duration of the burst selected. In this way, an estimate of the uterine electrical energy produced during a contraction can be established. Such a parameter will be useful in detecting contraction events, assessing the strength of uterine contraction events, and plotting said events in such a way as to be read just as is an intra-uterine pressure catheter device, and can therefore be used in the present invention in order that it performs as a replacement for intrauterine pressure catheter devices.

Another alternative technique for analysis of uterine activity is to plot the change in the magnitude of the power at one or more specific uterine frequencies versus time, or to plot the change in the sum of the magnitudes of the powers at various uterine frequencies versus time, the range of uterine frequencies of interest usually residing within from 0.001 Hz to 1.500 Hz, for example. Such a plot will be useful for detecting and plotting contraction events, plotting said events in such a way as to be read just as is a tocodynamometer, and can therefore be used in the present invention in order that it performs as a replacement for tocodynamometers.

Another technique that may be utilized is a fast wavelet transform technique. This technique could be adapted from that described in Cody, The Fast Wavelet Transform, Dr. Dobb's Journal (April 1992); Cody, A Wavelet Analyzer, Dr. Dobb's Journal (April 1993); and Cody, The Wavelet Packet Transform, Dr. Dobb's Journal (April 1994); for ECG, see A. Djohan, T. Q. Nguyen and W. Tompkins, "ECG Compression using Discrete Symmetric Wavelet Transform," International Conf. EMBS, September 1995; Sri-KrishnaAditya, Chee-Hung H. Chu, and Harold H. Szu, "Application of adaptive sub-band coding for noisy band-limited ECG signal processing", SPIE Proceedings Vol. 2762, pp. 376–387).

One objective of wavelet analysis, like Fourier analysis, is to re-express data in terms of frequency content (or the equivalent). Wavelet analysis belongs to a general set of approaches called time-frequency analysis. Unlike Fourier frequency analysis, time-frequency analysis determines the "instantaneous" frequency content at each time point and is more appropriate for signals whose frequency characteristics clearly change with time. The continuous wavelet transform essentially describes the signal in terms of all possible frequencies, or scales.

Once labor has begun, the EMG signal analysis method taught by the present invention will be useful in diagnosing, assessing treatment options, and in predicting the course of labor. This may also be combined with conventional clinical methods, such as intrauterine pressure measurement. The methods of EMG signal analysis taught by the present invention may also be useful postpartum in assessing the regression of uterine activity.

There are some disorders of uterine contractility or motility that occur outside pregnancy. One of these is dysmenorrhea. It is caused by cramping during parts of the menstrual cycle. Another important disorder is due to smooth muscle tumors ("fibroids" or leiomyomata) in the myometrium. This disorder tends to be hyperexcitable compared to normal myometerium and can be very painful. Often, women are treated with hormones to produce regression of these tumors. Functional regression of such tumors may be monitored and analyzed with the present invention. Other smooth muscle organs in both men and women such as bladder and bowel also show spontaneous activity that could be monitored and analyzed with the present invention.

Although described above in the context of discrete circuit elements such as envelope detectors, digital filters, etc., it should be appreciated that all or most of the illustrated blocks could be implemented with a suitably programmed data processor, such as a digital signal processor (DSP). Similarly, the various separate computer memories could all be contained within a single memory device or medium. While the invention has been particularly shown and described with respect to presently preferred embodiments thereof, it will be understood by those skilled in the art that changes in form and details may be made therein without departing from the scope and spirit of the invention.

While the foregoing is directed to various embodiments of the present invention, other and further embodiments can be devised without departing from the basic scope thereof. For example, the various methods and embodiments of the invention can be included in combination with each other to produce variations of the disclosed methods and embodiments. Discussion of singular elements can include plural elements and vice-versa. Claiming singular elements with the phrase comprising or variations thereof includes plural elements. Also, any directions shown or described such as "top," "bottom," "left," "right," "upper," "lower," and other directions and orientations are described herein for clarity in reference to the figures and are not to be limiting of the actual device or system or use of the device or system. The device or system can be used in a number of directions and orientations. Further, the order of steps or blocks can occur in a variety of sequences unless otherwise specifically limited. The various steps or blocks described herein can be combined with other steps or blocks, interlineated with the stated steps or blocks, and/or split into multiple steps or blocks. Similarly, elements have been described functionally and can be embodied as separate components or can be combined into components having multiple functions. Additionally, any headings herein are for the convenience of the reader and are not intended to limit the scope of the invention.

Further, any references mentioned in the application for this patent as well as all references listed in the information disclosure originally filed with the application are hereby incorporated by reference in their entirety to the extent such may be deemed essential to support the enabling of the invention(s). However, to the extent statements might be considered inconsistent with the patenting of the invention (s), such statements are expressly not meant to be considered as made by the Applicants.

What is claimed is:

1. A method for characterizing uterine electrical activity, comprising:
   a. applying an action potential measuring multi-polar arrangement of electrodes to an abdominal, vaginal or cervical surface of a patient;
   b. isolating a system from the patient for analog filtering and amplifying an electrical signal as appropriate to isolate desired frequency components of said signal from background noise in said signal;
   c. acquiring analog electrical uterine, maternal or fetal cardiac signals, fetal brain signals, or a combination thereof transmitted through said electrodes at a sampling frequency between about 0.5 and 1 kHz for a duration of time sufficient to record at least 3 bursts of action electrical potentials from said signals;
   d. removing unwanted signal components through a multi-channel noise elimination scheme to generate reduced noise signals;
   e. storing said reduced noise signals;
   f. using detection algorithms to detect one or more attributes of said uterine, maternal or fetal cardiac activity, fetal brain activity, or combination thereof that are present in said acquired signals;
   g. analyzing at least a portion of said activity, indicating parameters from at least one burst of the action potentials within the stored signals;
   h. characterizing said activity from said patient based on said parameter analysis;
   i. determining electrically when contractions occur;
   j. simulating data output of a tocodynamometer or an intra-uterine pressure catheter; and
   k. predicting when a patient will go into labor or delivery, or a combination thereof.

2. The method of claim 1, wherein simulating data output comprises simulating when contractions occur, plotting the contractions, displaying the strength of the contractions, or combinations thereof.

3. The method of claim 1, wherein isolating the system comprises isolating electrically or optically.

4. The method of claim 1, wherein removing unwanted signal components comprises using cross-correlation, auto-correlation, adaptive filtering, matched filtering, singular value decomposition, or combinations thereof.

5. The method of claim 1, wherein removing unwanted signal components further comprises determining phase relationships and modifying or maintaining said phase relationships between various channel combinations of the multi-polar arrangement of electrodes.

6. The method of claim 1, further comprising determining at least one of the following: frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis of said uterine, maternal or fetal cardiac or fetal brain signal traces, bursts, or groups or series of action potentials, or combinations thereof.

7. The method of claim 1, further comprising determining at least one of the following: frequency, duration, amplitude, power density spectrum, wavelet transforms, Fourier transforms, spectral-temporal mapping, complexity, chaos, fractals, zero-crossings, randomness, non-linearity, likelihood ratios, and statistical evaluations, Wigner-Ville or Heisenberg-Gabor analysis, or other joint time-frequency analysis of one or more individual action potentials in at least one of said uterine, maternal or fetal cardiac or fetal brain signal traces, bursts, or groups or series of action potentials, or combinations thereof.

8. The method of claim 1, further comprising using "Fourier" analysis techniques to determine at least one attribute of the electrical signals, comprising at least one of the following:
   a. determining the mean frequency of a plurality of action potentials in at least one of said uterine electrical bursts or maternal and fetal cardiac and fetal brain signals;
   b. determining the starting frequency of action potentials in at least one of said uterine electrical bursts or maternal and fetal cardiac and fetal brain electrical signals;
   c. determining the ending frequency of action potentials in at least one of said uterine electrical bursts or maternal and fetal cardiac and fetal brain signals;
   d. determining the mean frequency at which peaks occur in the power density spectrum of action potentials in at least one of said uterine electrical bursts or maternal and fetal cardiac and fetal brain signals;
   e. determining the sum of the power across various frequencies in at least one of said uterine electrical bursts or maternal and fetal cardiac and fetal brain signals;
   f. determining the power magnitude of various peaks in the power density spectrum of at least one of said uterine electrical bursts or maternal and fetal cardiac and fetal brain signals;
   g. determining the spectral-temporal map of one or more frequencies of at least one of said uterine electrical bursts or maternal and fetal cardiac and fetal brain signals;
   h. determining the energy of at least a portion of said acquired uterine, maternal, or fetal cardiac or fetal brain electrical signals or combinations thereof in a given range of frequencies by calculating the power of the portion of the signals corresponding to the range of frequencies desired and multiplying by the duration of that portion of the signal.

9. The method of claim 1, further comprising:
   a. determining the rate of rise of amplitude in at least one action potential in at least one of said uterine electrical bursts or maternal and fetal cardiac and fetal brain signals; and
   b. determining the rate of fall of amplitude in at least one action potential in at least one of said uterine electrical bursts or maternal and fetal cardiac and fetal brain signals.

10. The method of claim 1, further comprising using "wavelet" analysis techniques to determine one or more attributes of the electrical signals, comprising at least one of the following:
    a. determining wavelet coefficients in at least one of said uterine electrical bursts or maternal and fetal cardiac and fetal brain signals;
    b. determining spline functions in at least one of said uterine electrical bursts or maternal and fetal cardiac and fetal brain signals;
    c. determining scales in at least one of said uterine electrical bursts or maternal and fetal cardiac and fetal brain signals; and
    d. determining percent-energy distribution across wavelet scales in at least one of said uterine electrical bursts or maternal and fetal cardiac and fetal brain signals.

11. The method of claim 1, further comprising using "complexity" or "randomness" analysis techniques to determine one or more attributes of the electrical signals, comprising at least one of the following:
    a. determining eigenvalues and eigenfunctions in at least one of said uterine electrical bursts or maternal and fetal cardiac and fetal brain signals;
    b. determining primitive and exhaustive histories in at least one of said uterine electrical bursts or maternal and fetal cardiac and fetal brain signals; and
    c. determining Limpel-Ziv (LZ) complexity measures in at least one of said uterine electrical bursts or maternal and fetal cardiac and fetal brain signals.

12. The method of claim 1, further comprising using "zero-crossing" analysis techniques to determine at least one attribute of the electrical signals, comprising at least one of the following:
    a. determining zeroth-order, first-order, or higher-order crossing counts in at least one of said uterine electrical bursts or maternal and fetal cardiac and fetal brain signals.

13. The method of claim 1, further comprising using "fractal" analysis techniques to determine at least one attribute of the electrical signals, comprising at least one of the following:
    a. determining the Hurst exponent for range/standard deviation ("R/S"), power spectrum, roughness-lengths, variograms, or wavelets methods, or combinations thereof, in at least one of said uterine electrical bursts or maternal and fetal cardiac and fetal brain signals;
    b. determining the fractal dimension for R/S, power spectrum, roughness-lengths, variograms, or wavelets methods, or combinations thereof, in at least one of said uterine electrical bursts or maternal and fetal cardiac and fetal brain signals;
    c. determining beta values for R/S, power spectrum, roughness-lengths, variograms, or wavelets methods, or combinations thereof, in at least one of said uterine electrical bursts or maternal and fetal cardiac and fetal brain signals.

14. The method of claim 1, further comprising using "nonlinearity" and "chaos" analysis techniques to determine one or more attributes of the electrical signals, comprising at least one of the following:
   a. determining the entropy and approximate entropy in at least one of said uterine electrical bursts or maternal and fetal cardiac and fetal brain signals;
   b. determining Kolmogorov-Smirnov statistics in at least one of said uterine electrical bursts or maternal and fetal cardiac and fetal brain signals; and
   c. determining the chaoticity in at least one of said uterine electrical bursts or maternal and fetal cardiac and fetal brain signals.

15. The method of claim 1, further comprising using "likelihood ratios" analysis techniques to determine at least one attribute of the electrical signals, comprising:
   a. determining the likelihood ratios and local generalized likelihood ratios using adaptive cumulative sums and dynamic cumulative sums in at least one of said uterine electrical bursts or maternal and fetal cardiac and fetal brain signals.

16. The method of claim 1, further comprising using statistical analysis techniques to determine one or more attributes of the electrical signals, comprising:
   a. determining the means, standard deviations, variances, expected values, discreet or continuous random variables or ratios or functions of at least one of said statistical techniques in at least one of said uterine electrical bursts or maternal and fetal cardiac and fetal brain signals.

17. The method of claim 1, further comprising examining one or more trends in uterine activity indicating parameters over time.

18. The method of claim 17, further comprising displaying one or more trends in uterine activity indicating parameters over time.

19. The method of claim 17, further comprising predicting future uterine activity based upon one or more identified trends of examined uterine activity indicating parameters.

20. The method of claim 19, wherein said predicting future uterine activity comprises identifying situations in which treatment for pharmacologically inducing or inhibiting labor in said patient may be indicated.

21. The method of claim 19, wherein said predicting future uterine activity comprises:
   a. comparing identified trends of a patient's examined uterine activity with trend data collected from other patients in order to identify matching trends; and
   b. predicting future uterine activity for a patient under examination based upon the trend behavior shown in the matching trends.

22. The method of claim 21, wherein said predicting is performed with the use of an expert system.

23. The method of claim 1, wherein said detection further comprises detecting the contraction of abdominal muscles in the patient.

24. The method of claim 1, further comprising determining joint time-frequency characteristics of said frequency components of bursts of uterine action potentials and maternal and fetal cardiac and fetal brain electrical signals.

25. The method of claim 1, further comprising monitoring a patient trans-abdominally, trans-vaginally, trans-cervically, or a combination thereof.

26. The method of claim 25, further comprising:
   a. evaluating uterine activity;
   b. simultaneously determining maternal and fetal heart activity;
   c. simultaneously monitoring said fetal brain activity.

27. The method of claim 26, wherein monitoring said fetal brain activity comprises monitoring alpha, beta, theta, delta brain waves, or combinations thereof, and further comprising determining the frequency, amplitude and morphology of such brain waves.

28. The method of claim 26, wherein maternal and fetal heart activity comprises QRST complexes, heart rate, or a combination thereof.

29. The method of claim 1, further comprising:
   a. stimulating a vagina of said patient while said uterine, maternal and fetal cardiac, and fetal brain signals are being stored; and
   b. diagnosing labor as a function of said analysis of uterine activity.

30. The method of claim 29, further comprising plotting contractions, plotting contraction strength, assessing maternal and fetal heart activity, and fetal brain activity, and accurately predicting labor and delivery, without the need for using a tocodynamometer or an intra-uterine pressure catheter.

31. The method of claim 1, further comprising generating three dimensional mesh plots of said power density spectral characteristics, said mesh plots displaying energy levels versus frequency versus time of pregnancy.

32. A system for recording and analyzing uterine electrical activity for the abdominal, cervical or vaginal surface, comprising:
   a. an arrangement of at least three electrodes forming a multi-polar arrangement adapted to measure electrical signals due to action potentials emitted from an abdominal, vaginal, or cervical surface of a patient under analysis to establish uterine, maternal and fetal cardiac, and fetal brain signals and each electrode further adapted to conduct an analog signal indicative of said action potentials, each electrode-pair being identified with one channel of data;
   b. at least one analog filter adapted to remove unwanted signal components from the uterine, maternal and fetal cardiac, and fetal brain signals;
   c. at least one differential, isolated, analog amplifier electrically coupled to said electrodes to receive and amplify signals indicative of said action potentials measured by said electrodes;
   d. at least one analog to digital converter adapted to generate digital signals from the analog signals produced by the amplifiers;
   e. at least one memory comprising sufficient storage capacity to store data resulting from a sampling of electrical signals at a sampling frequency of at least 100 Hz from a single patient for at least 1 hour, said memory adapted to receive a digital input from said analog to digital converter;
   f. a computer programmed to import electrical signal data from multiple channels, or multiple differential signals from multiple electrode-pairs, formed from an array of said multi-polar arrangement of electrodes, and to perform mathematical functions on at least two of the potentials measured to generate multiple channels of data which are the result of at least one mathematical combination of said potentials from said mathematical functions;

g. said computer programmed to perform multi-channel filtering on at least one of the channels of data to remove unwanted noise components common to one or more channels;

h. said computer programmed to analyze frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis on the uterine, cardiac, and brain signals acquired, said computer further being adapted to characterize uterine, maternal and fetal cardiac, and fetal brain activity based upon said analysis.

33. The system of claim 32, wherein said system is adapted to plot contractions, plot contraction strength, assess maternal and fetal heart activity, and fetal brain activity, and accurately predict labor and delivery, without the need for using a tocodynamometer or an intra-uterine pressure catheter.

34. The system of claim 32, wherein said multi-channel filtering comprises matched filtering, adaptive filtering, auto-correlation, cross-correlation filtering, singular value decomposition techniques, or combinations thereof.

35. The system of claim 32, wherein said computer is adapted to determine and modify or maintain phase relationships between multiple channel combinations to remove said unwanted noise components.

36. The system of claim 32, wherein one or more of said mathematical functions are optionally chosen by an operator operating said computer.

37. The system of claim 32, wherein said mathematical functions are programmed into said computer for automatic execution thereof.

38. The system of claim 32, wherein said computer is adapted to identify abdominal muscle contractions.

39. The system of claim 32, wherein said memory is adapted to store said electrical signals in discrete, predetermined frequency ranges.

40. The system of claim 32, wherein said computer is further adapted to determine a mean frequency, starting frequency, and ending frequency of a plurality of action potentials.

41. The system of claim 32, wherein said electrical signal measuring electrodes comprise needle electrodes, surface electrodes, vaginally-placed, or cervically-located electrodes, or a combination thereof.

42. The system of claim 32, further comprising a monitor coupled to said computer, said monitor adapted to display at least a portion of said electrical signals.

43. A remote uterine monitoring system for remotely characterizing uterine activity, comprising:

a. at least three electrodes forming a multi-polar arrangement adapted to measure electrical signals of action potentials emitted from an abdominal, vaginal, or cervical surface of a patient under analysis to establish uterine, maternal and fetal cardiac and fetal brain signals and further adapted to emit an analog signal indicative of action potentials measured by said electrodes;

b. an isolation system comprising analog filters adapted to remove unwanted signal components from the uterine, maternal and fetal cardiac, and fetal brain signals;

c. at least one analog differential amplifier coupled to said electrodes, isolated from the patient optically, electrically, or by other standard means, and adapted to receive and amplify signals indicative of action potentials measured by said electrodes;

d. at least one analog to digital converter adapted to produce digital signals from the analog signals produced by the amplifiers;

e. a computer programmed to import electrical signal data from multiple channels, or multiple differential signals from multiple electrode-pairs, formed from an array of said multi-polar arrangement of electrodes, and to perform mathematical functions on two or more of the channels to generate channels of data, which are the result of such mathematical combination of said potentials;

f. said computer adapted to perform multi-channel filtering on said channels of data to remove unwanted noise components common to one or more channels;

g. said computer programmed to analyze the frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis on the uterine, cardiac, and brain signals acquired, said expert system further being adapted to characterize maternal uterine, maternal and fetal cardiac, and fetal brain activity based upon said analysis;

h. at least one data transmission system, coupled to said computer, adapted to transmit uterine, maternal and fetal cardiac, and fetal brain signals, processed or unprocessed, to a remote location from said computer via a telecommunications link;

i. at least one remote analog to digital converter coupled to said data transmission system to receive an analog input from said amplifier indicative of action potentials measured by said electrodes;

j. at least one memory comprising sufficient storage capacity to store data resulting from a sampling of trans-abdominal, trans-vaginal, trans-cervical electrical signals, or a combination thereof, at a sampling frequency of at least 100 Hz from a single patient for at least 1 hour, said memory adapted to receive a digital input from said analog to digital converter indicative of action potential signals received by said converter;

k. at least one receiver adapted to collect the uterine, cardiac, or brain signals, processed or unprocessed, which is transmitted from said computer at the site of the patient; and l. at least one remote computer located remote from the patient and coupled to said receiver to import received data from the site of the patient and programmed to analyze the frequency, duration, amplitude, power density spectrum, wavelet transforms, Fourier transforms, rate of rise and fall of signals, spectral-temporal mapping, complexity, chaos, fractals, zero-crossings, randomness, non-linearity, likelihood ratios, statistical evaluations, Wigner-Ville or Heisenberg-Gabor analysis, or other joint time-frequency analysis on the uterine, cardiac, and brain signals acquired, said remote computer further being capable of characterizing maternal uterine, maternal and fetal cardiac, and fetal brain activity based upon said analysis.

44. The system of claim 43, wherein said system is adapted to plot contractions, plot contraction strength, assess maternal and fetal heart activity, and fetal brain activity, and accurately predict labor and delivery, without the need for using a tocodynamometer or an intra-uterine pressure catheter.

45. The system of claim 43, wherein said filtering comprises matched filtering, adaptive filtering, auto-correlation and/or cross-correlation, or singular value decomposition filtering techniques, or combinations thereof.

46. The system of claim 43, wherein at least one of said computers is adapted to determine and modify or maintain phase relationships between various channel combinations to reduce said unwanted noise components.

47. The system of claim 43, wherein said telecommunications link comprises a wireless communication link.

* * * * *